(12) United States Patent
Vankoevering et al.

(10) Patent No.: US 10,905,556 B2
(45) Date of Patent: Feb. 2, 2021

(54) TEGMEN PLATE PROSTHESIS AND METHODS FOR MANUFACTURING AND USING THE SAME

(71) Applicant: The Regents of the University of Michigan, Ann Arbor, MI (US)

(72) Inventors: Kyle Vankoevering, Ann Arbor, MI (US); Sameer Ahmed, Ann Arbor, MI (US); Henry Alexander Arts, Ann Arbor, MI (US); Glenn Edward Green, Gregory, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 70 days.

(21) Appl. No.: 15/368,083

(22) Filed: Dec. 2, 2016

(65) Prior Publication Data
US 2017/0156868 A1    Jun. 8, 2017

Related U.S. Application Data

(60) Provisional application No. 62/263,289, filed on Dec. 4, 2015.

(51) Int. Cl.
*A61F 2/28* (2006.01)
*B33Y 80/00* (2015.01)
(Continued)

(52) U.S. Cl.
CPC ............ *A61F 2/2875* (2013.01); *A61B 34/10* (2016.02); *A61F 2/18* (2013.01); *A61F 2/30942* (2013.01);
(Continued)

(58) Field of Classification Search
CPC .. A61F 2/2875; A61F 2/30942; A61F 11/004; A61B 17/8085
(Continued)

(56) References Cited

U.S. PATENT DOCUMENTS 5,501,706 A      3/1996  Arenberg
7,833,253 B2 *  11/2010  Ralph ................. A61B 17/688
                                                       403/397
(Continued)

FOREIGN PATENT DOCUMENTS

WO          03030787 A1     4/2003

OTHER PUBLICATIONS

Cohen J. et al. "Creation of a 3D printed temporal bone model from clinical CT data", American Journal of Otolaryngology, vol. 36, Issue 5, p. 619-624, Sep.-Oct. 2015.
(Continued)

*Primary Examiner* — Marcia L Watkins
(74) *Attorney, Agent, or Firm* — Harness, Dickey & Pierce, P.L.C.

(57) ABSTRACT

Prosthetic tegmen plates are provided. The prosthetic tegmen plates include a body that defines at least one engagement surface that substantially conforms to a region of a corresponding surface of a subject's temporal bone having a tegmen defect. The prosthetic tegmen plates are configured to cover the tegmen defect. Methods for manufacturing prosthetic tegmen plates by additive manufacturing and surgically implanting prosthetic tegmen plates are also provided.

30 Claims, 18 Drawing Sheets

(51) Int. Cl.
  *A61F 2/18* (2006.01)
  *A61B 34/10* (2016.01)
  *A61F 2/30* (2006.01)
(52) U.S. Cl.
  CPC ......... *B33Y 80/00* (2014.12); *A61B 2034/105* (2016.02); *A61B 2034/108* (2016.02); *A61F 2/3094* (2013.01); *A61F 2002/183* (2013.01); *A61F 2002/30062* (2013.01); *A61F 2002/30677* (2013.01); *A61F 2002/30948* (2013.01)
(58) Field of Classification Search
  USPC ..... 623/11.11, 16.11, 17.19, 17.18; 606/285, 606/903
  See application file for complete search history.

(56) References Cited

U.S. PATENT DOCUMENTS

| | | | |
|---|---|---|---|
| 8,211,180 B2 | 7/2012 | Keller et al. | |
| 2003/0216669 A1 | 11/2003 | Lang et al. | |
| 2004/0015070 A1 | 1/2004 | Liang et al. | |
| 2012/0010711 A1* | 1/2012 | Antonyshyn | A61F 2/2875 623/16.11 |
| 2013/0245801 A1 | 9/2013 | Schroeder | |
| 2017/0239054 A1* | 8/2017 | Engstrand | A61F 2/2875 |
| 2017/0296239 A1 | 10/2017 | Cordaro | |
| 2018/0055640 A1* | 3/2018 | Gordon | A61N 1/0526 |

OTHER PUBLICATIONS

Greene, A.K. et al., "Repair of tegmen defect using cranial particulate bone graft", American Journal of Otolaryngology, vol. 36, Issue 2, p. 292-295, Mar.-Apr. 2015.

International Search Report and Written Opinion of International Searching Authority issued in PCT/US2016/064773, dated Mar. 13, 2017.

Extended European Search Report for European Patent Application No. 16871640.5 dated Jul. 29, 2019, 11 pages.

Marchioni, Daniele et al., "Combined Approach for Tegmen Defects Repair in Patients with Cerebrospinal Fluid Otorrhea or Herniations: Our Experience," J. Neurol. Surg. B. (2014) 75, pp. 279-287 (Published online: May 2, 2014); DOI: 10.1055/s-0034-1371524.

Savva, Athanasia et al., "Management of Cerebrospinal Fluid Leaks Involving the Temporal Bone: Report on 92 Patients," The Laryngoscope 113, 1 (2003), pp. 50-56; DOI: 10.1097/00005537-200301000-00010.

Dobozi, M., "Surgical Anatomy of the Geniculate Ganglion." Acta Oto-Laryngologica, vol. 80, No. 1-6, pp. 116-119 (1975).

Hamzaoğlu, Vural et al., "Radioanatomic Assessment of the Geniculate Ganglion Dehiscence and Dimension: A Cadaveric Study." World Neurosurgery, vol. 134, pp. e913-e919 (2020).

Isaacson, Brandon et al., "The Radiographic Prevalence of Geniculate Ganglion Dehiscence in Normal and Congenitally Thin Temporal Bones." Otology & Neurotology, vol. 28, pp. 107-110 (2006).

* cited by examiner

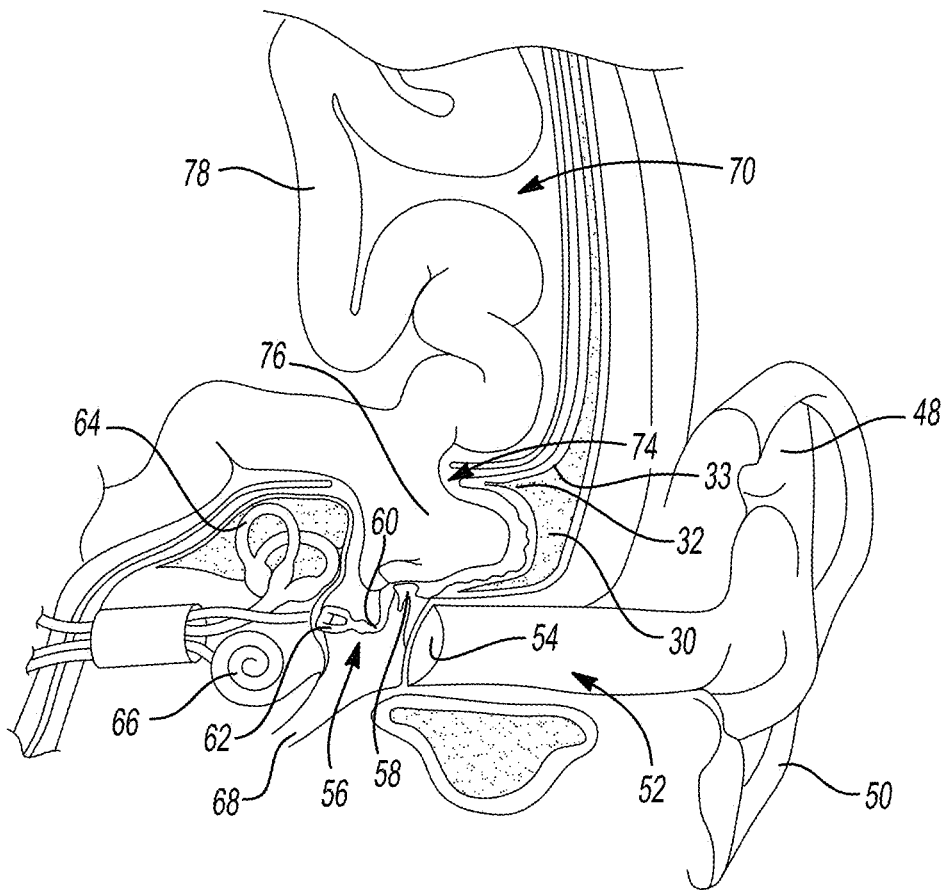
_Fig-4_
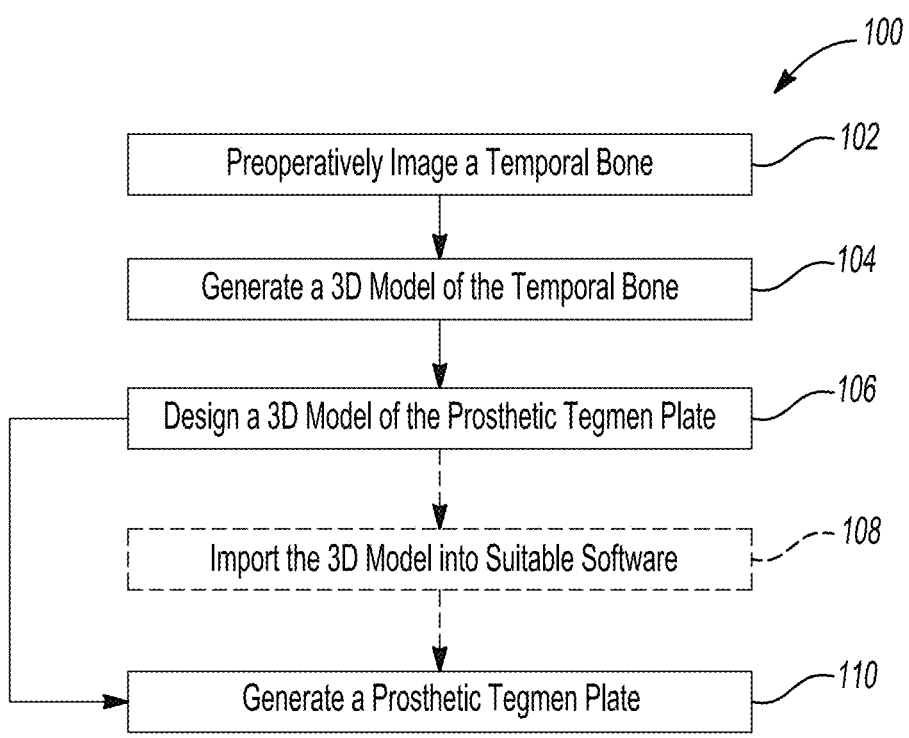
_Fig-5_

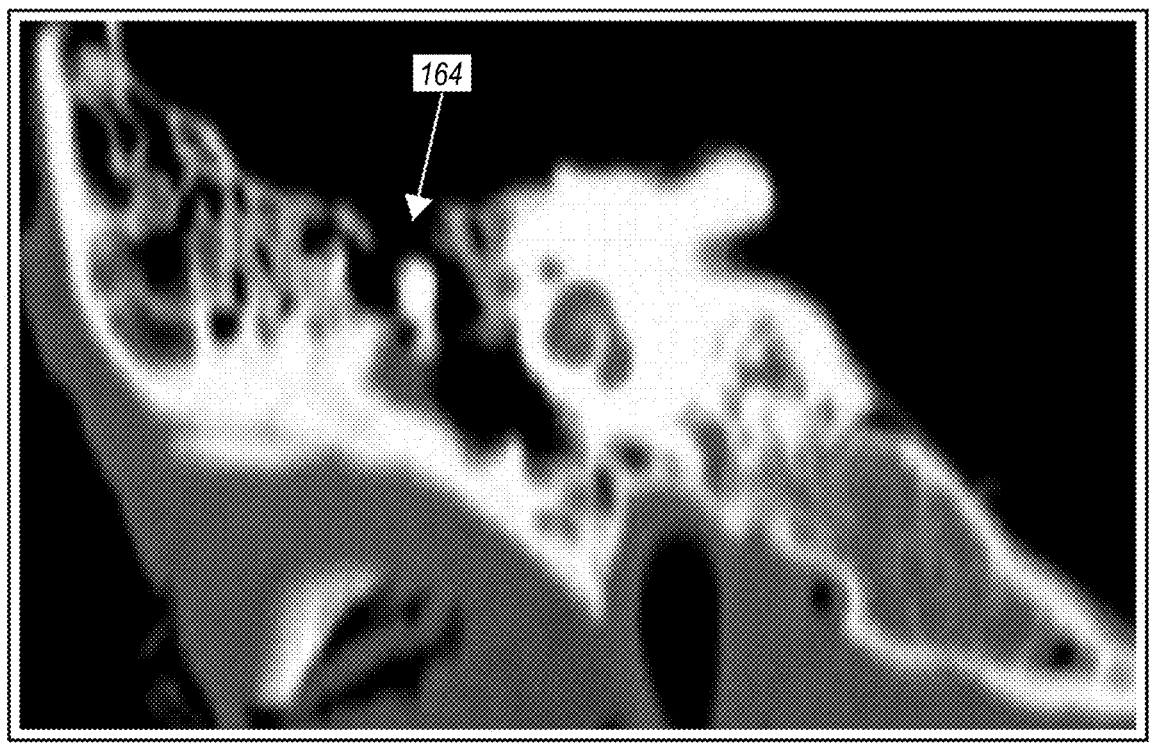
Fig-14
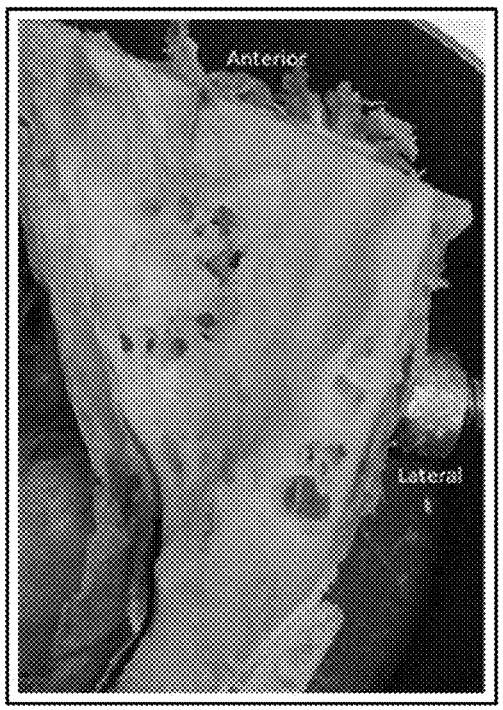 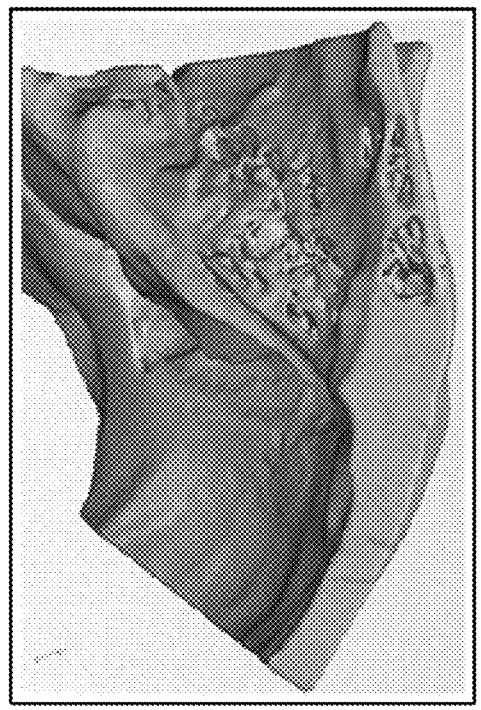
Fig-15A          Fig-15B

TEGMEN PLATE PROSTHESIS AND METHODS FOR MANUFACTURING AND USING THE SAME

CROSS-REFERENCE TO RELATED APPLICATIONS

This application claims the benefit and priority of U.S. Application Ser. No. 62/263,289 filed on Dec. 4, 2015. The entire disclosure of the above application is incorporated herein by reference.

FIELD

The present disclosure relates to methods for manufacturing prosthetic tegmen plates for implanting in subjects in need thereof and tegmen plate prostheses manufactured therefrom

BACKGROUND

This section provides background information related to the present disclosure which is not necessarily prior art.

The human cranium comprises eight cranial bones that define a cranial cavity. The cranial bones include a frontal bone, two parietal bones, a sphenoid bone, two temporal bones, an occipital bone, and an ethmoid bone. The base or floor of the cranium is divided into three fossae; an anterior cranial fossa, a middle cranial fossa, and a posterior cranial fossa. In particular, the anterior cranial fossa includes the frontal bone, the ethmoid bone, and a lesser wing of the sphenoid bone; the middle cranial fossa includes a greater wing of the sphenoid bone, and an anterior portion of the temporal bones; and the posterior cranial fossa includes a posterior portion of the temporal bones, and the occipital bone. The parietal bones border the occipital bone, temporal bones, sphenoid bone, and frontal bone, and form the sides and roof of the cranium.

Inferior to a portion of the middle cranial fossa is a tympanic cavity, which houses bones of the middle ear, and a mastoid, which is an air cell system with variable pneumatization in different subjects or patients. A portion of the temporal bone in the middle cranial fossa, the tegmen is a thin layer of bone that separates the cranial cavity from both the tympanic cavity and the mastoid, both of which are located inferior to the brain. The tegmen is divided into an anterior component, the tegmen tympani, and a posterior component, the tegmen mastoideum. Accordingly, a superior surface of the tegmen tympani borders a temporal lobe of the brain and an inferior surface of the tegmen tympani defines a roof of the middle ear. Similarly, a superior surface of the tegmen mastoideum borders the temporal lobe of the brain and an inferior surface of the tegmen mastoideum defines a roof of the mastoid. This region of the temporal bone is one of the most anatomically complex regions of the human anatomy.

Defects, such as small holes, in the tegmen tympani and/or tegmen mastoideum can result in otologic complaints, such as decreased hearing, vestibular complaints, such as dizziness (including imbalance, lightheadedness, and vertigo), and cerebrospinal fluid (CSF) leaks. Often, such defects are simply observed and monitored. To repair some defects, such as small, lateral defects, transmastoid approaches may be pursued, such as repairing the defect from below. For example, holes in the tegmen mastoideum may be "plugged" from below after drilling an opening into the mastoid. Another approach for repairing tegmen defects requires accessing the tegmen through a middle fossa craniotomy. In this approach, a bone window is carved through the parietal bone, the temporal lobe of the brain is retracted to expose the defect, and a piece of bone or cartilage (typically autologous) is carved and laid over the superior surface of the tegmen to span the defect. The piece of bone or cartilage is cemented into place and sealed with a layer of fascia. Another repair option is to implant an alloplastic material (such as titanium mesh), to similarly span defects in the tegmen.

Due to being in a region of complex anatomy, repairing defects of the tegmen is challenging and provides modest results. Opening a window to the middle cranial fossa, retracting the brain, sculpting a piece of tissue (or alloplastic material), and cementing the tissue (or alloplastic material) in place is difficult and typically takes from four to eight hours to complete during a surgical procedure. Accordingly, alternative methods for repairing tegmen defects are needed.

SUMMARY

This section provides a general summary of the disclosure, and is not a comprehensive disclosure of its full scope or all of its features.

The present technology provides a method of implanting a prosthetic tegmen plate in a subject having a tegmen defect. The method includes implanting a prosthetic tegmen plate in the subject so as to cover the tegmen defect. The prosthetic tegmen plate has a mating surface complementary to at least a portion of the subject's temporal bone including the tegmen defect. The prosthetic tegmen plate is generated from a three dimensional (3D) model created from preoperative images of the subject's temporal bone, so that the mating surface substantially conforms to the corresponding surface of the subject's temporal bone after the implanting.

In certain aspects, implanting the prosthetic tegmen plate in the subject includes locating the prosthetic tegmen plate in the subject such that the mating surface nestingly mates with the corresponding surface of the subject's temporal bone without requiring any anchoring with hardware or adhesives, In certain aspects, the method further includes generating the prosthetic tegmen plate before the implanting. The generating includes creating a first three dimensional (3D) model of the tegmen defect from preoperative images of the subject's temporal bone, creating a second 3D model of the prosthetic tegmen plate complementary to the first 3D model, and additive manufacturing the prosthetic tegmen plate from the second 3D model, wherein the mating surface of the prosthetic tegmen plate is complementary to at least a portion of the subject's temporal bone comprising the tegmen based on the first 3D model.

In certain aspects the preoperative images are created by magnetic resonance imaging (MRI), computed tomography (CT), positron emission tomography (PET), ultrasound, X-ray, or a combination thereof.

In certain aspects, the prosthetic tegmen plate is generated by 3D printing.

In certain aspects, the implanting includes creating a window through a parietal bone of the subject, exposing the tegmen defect, and implanting the prosthetic tegmen plate on the subject's temporal bone, such that the prosthetic tegmen plate covers the subject's tegmen defect.

In certain aspects, the implanting further includes sealing the prosthetic tegmen implant in place with a layer of the subject's fascia.

In certain aspects, the prosthetic tegmen plate further includes at least one supplemental component selected from the group consisting of a growth factor, a suspension of cells, an anti-inflammatory agent, an antimicrobial agent, a blood fraction, and combinations thereof.

In certain aspects, the tegmen defect is associated with a congenital defect, intracranial hypertension, pulsatile tinnitus, tullio phenomenon, encephalocele, a cerebrospinal fluid (CSF) leak, or meningitis.

In certain aspects, the tegmen defect is a defect in the subject's tegmen tympani, tegmen mastoideum, or combination thereof.

The present technology also provides a method of manufacturing a prosthetic tegmen implant for implanting in a subject in need thereof. The method includes generating a first three dimensional (3D) model of at least a portion of the subject's temporal bone having the tegmen defect from preoperative images of the subject's temporal bone; designing a second 3D model of a prosthetic tegmen plate including a mating surface complimentary to at least a portion of the subject's temporal bone having the tegmen defect; and generating the prosthetic tegmen plate having a mating surface that substantially conforms to a corresponding surface of the subject's temporal bone.

In certain aspects, the generating of the first 3D model and the second 3D model occurs by use of image processing software.

In certain aspects, generating a prosthetic tegmen plate includes generating a prosthetic tegmen plate by additive manufacturing.

In certain aspects, the designing a second 3D model of a prosthetic tegmen plate includes drawing a two dimensional outline of the prosthetic tegmen implant over the tegmen defect on the first 3D model, the two dimensional outline defining edges of the prosthetic tegmen implant, and offsetting the two dimensional outline to generate a virtual 3D tegmen plate construct having a thickness of at least about 1 mm.

In certain aspects, the method also includes, prior to the offsetting, elevating a central portion of the two dimensional outline off of the tegmen defect to a height of from greater than or equal to about 0.05 to less than or equal to about 1 mm, wherein the two dimensional outline has an unmodified portion that extends inward from the edges toward the central portion and the unmodified portion having a length of at least about 2 mm.

Additionally, the present technology provides a prosthetic tegmen plate. The prosthetic tegmen plate includes a body formed by additive manufacturing having a biocompatible material. The body defines at least one engagement surface that substantially conforms to a region of a corresponding surface of a subject's temporal bone having a tegmen defect. The prosthetic tegmen plate is configured to cover the tegmen defect.

In certain aspects, the prosthetic tegmen plate has a thickness of less than or equal to about 5 mm.

In certain aspects, the biocompatible material is selected from the group consisting of: a biocompatible polymer, a ceramic, a metal, and combinations thereof.

In certain aspects, the biocompatible material is a non-bioresorbable polymer selected from the group consisting of a polyaryl ether ketone (PAEK), poly(methyl acrylate) (PMA), poly(methyl methacrylate) (PMMA), polyetherimide (PEI), polysulfone, polyphenolsulfone, copolymers thereof, and combinations thereof.

In certain aspects, the PAEK is selected from the group consisting of polyetherketone (PEK), polyether ketone ketone (PEKK), polyether ether ketone (PEEK), polyether ether ketone ketone (PEEKK), polyether ketone ether ketone ketone (PEKEKK), and combinations thereof.

In certain aspects, the biocompatible material is polyether ketone ketone (PEKK).

In certain aspects, the biocompatible material is a bioresorbable biocompatible polymer.

In certain aspects, the biocompatible material further includes at least one component selected from the group consisting of: a growth factor, a suspension of cells, an anti-inflammatory agent, an antimicrobial agent, a blood fraction, and combinations thereof.

In certain aspects, the biocompatible material is a bioresorbable polymer selected from the group consisting of poly lactic acid (PLA), poly glycolic acid (PGA), poly lactic co-glycolic acid (PLGA), polyhydroxybutyrate (PHB), polyhydroxyvalerate (PHV), poly(desaminotyrosyl-tyrosine ethyl carbonate) (poly(DTE-carbonate)), polycaprolactone, polyanhydrides, polyorthoesters, copolymers thereof, and combinations thereof.

In certain aspects, the biocompatible material comprises a polysaccharide selected from the group consisting of starch, alginate, hyaluronic acid, and combinations thereof, or a protein selected from the group consisting of collagen, fibrin, silk, and combinations thereof.

In certain aspects, the prosthetic tegmen plate nestingly mates to a corresponding surface of the subject's temporal bone in only a single orientation.

In certain aspects, the body includes an elevated central portion that is configured to be elevated over the tegmen defect by a height of from greater than or equal to about 0.05 to less than or equal to about 1 mm, and an unmodified portion that extends inward from edges defined by the body toward the central portion, the unmodified portion having a length of at least about 2 mm.

In certain aspects, the unmodified portion comprises the at least one engagement surface.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 4 is an illustration of an exemplary tegmen defect;

FIG. 5 is a method for manufacturing a prosthetic tegmen plate;

FIG. 14 is a coronal image from a high resolution CT scan of a right cadaveric temporal bone with a large tegmen defect overlying the head of a malleus;

FIG. 15A is a photograph of a cadaveric temporal bone;

FIG. 15B is a model representation of the temporal bone shown in FIG. 15A demonstrating high fidelity and exact modeling of tegmen floor contours with mild overestimation of defect sizes;

Corresponding reference numerals indicate corresponding parts throughout the several views of the drawings.

DETAILED DESCRIPTION

Figure 1:
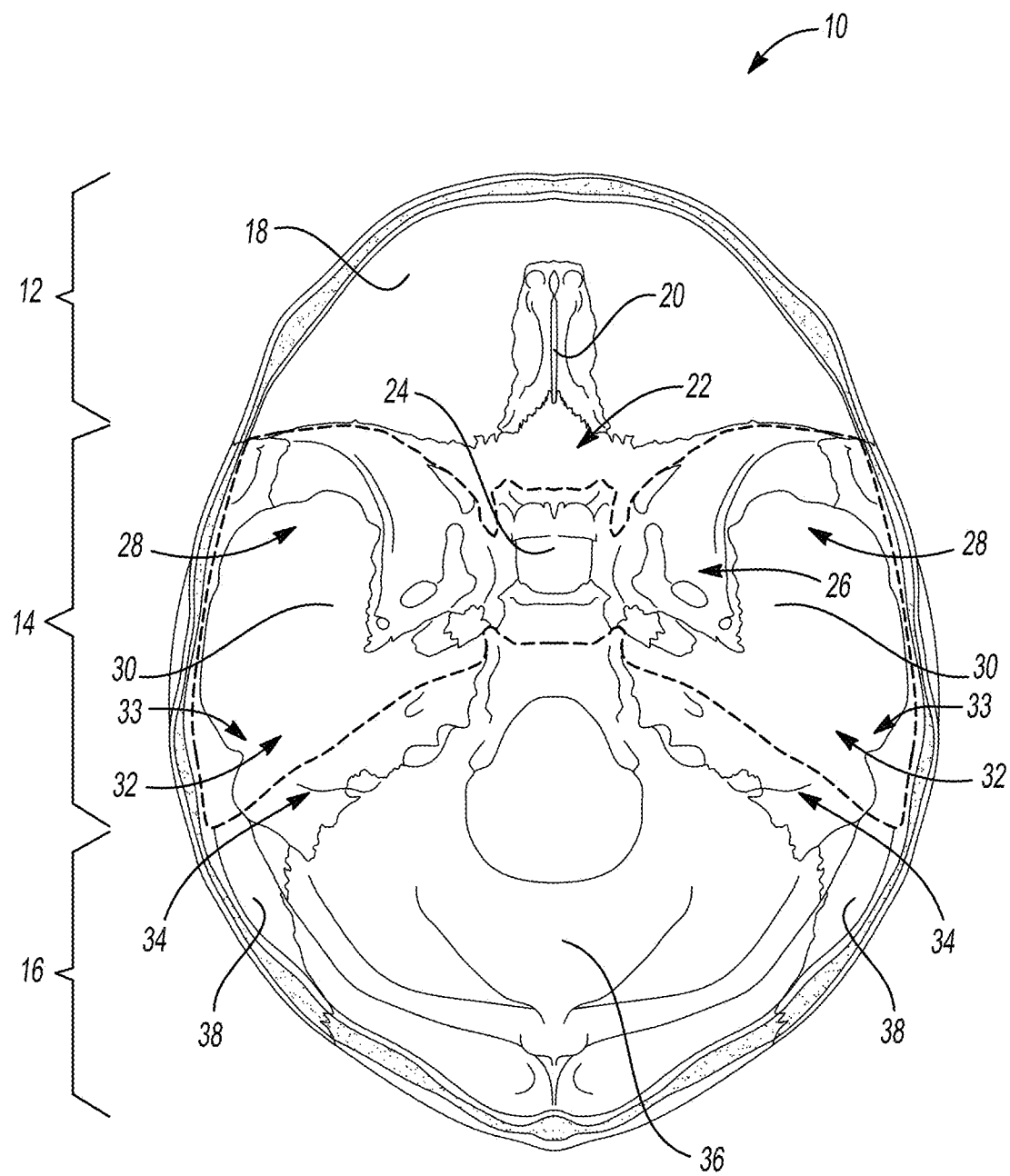
FIG. 1 shows an illustration of a cross section of a cranium taken along an axial plane to expose a cranial base.

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters.

In addition, disclosure of ranges includes disclosure of all values and further divided ranges within the entire range, including endpoints and sub-ranges given for the ranges. As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B.

Example embodiments will now be described more fully with reference to the accompanying drawings.

As discussed above, the region about the middle cranial fossa and the tympanic cavity is among the most complicated regions of the human anatomy. FIG. 1 shows an illustration of a cross section of a cranium taken along an axial plane to expose a cranial base 10. The cranial base 10 includes an anterior cranial fossa 12, middle cranial fossa 14, and posterior cranial fossa 16. The anterior cranial fossa 12 includes a frontal bone 18, an ethmoid bone 20, and a lesser wing 22 of a sphenoid bone 24. The middle cranial fossa 14 includes a greater wing 26 of the sphenoid bone 24, and anterior portions 28 of two temporal bones 30. The anterior portions 28 of the temporal bones 30 comprise tegmen tympani 32 and the tegmen mastoideum 33. The posterior cranial fossa 16 includes a posterior portion 34 of the temporal bones 30, and the occipital bone 36. A pair of parietal bones 38 border the occipital bone 36, temporal bones 30, sphenoid bone 24, and frontal bone 18, and form the sides and roof of the cranium.

Figure 2:
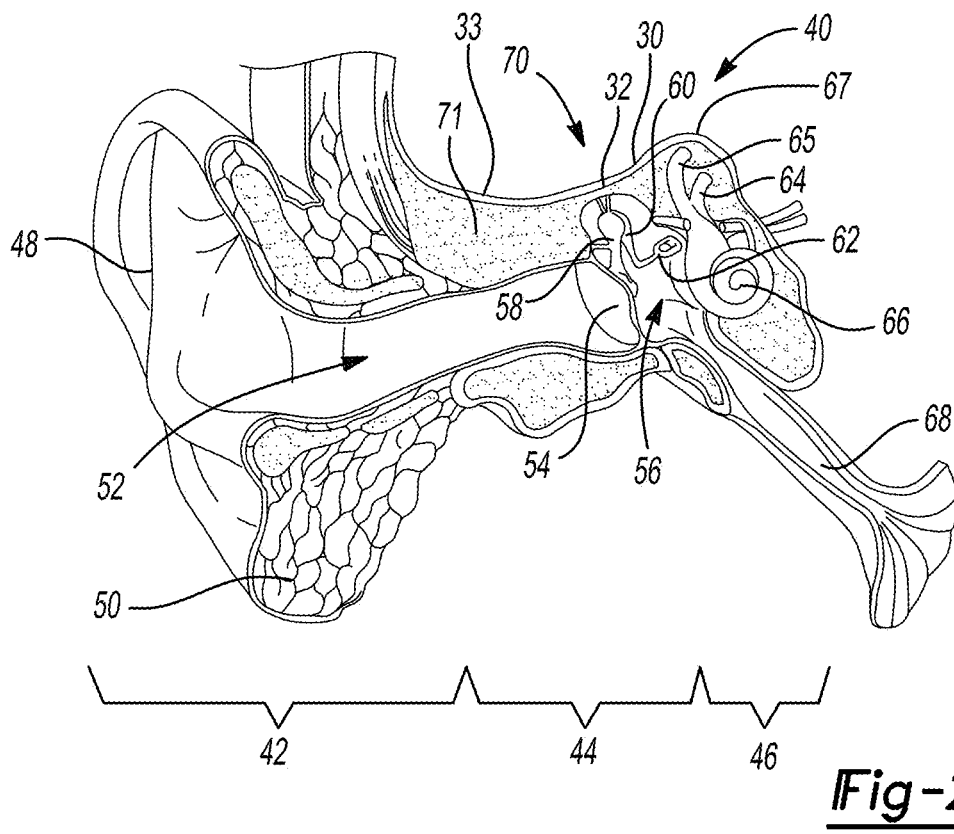
FIG. 2 shows an illustration of the anatomy of a human ear.

FIG. 2 shows an illustration of the anatomy of a human ear 40. The ear 40 comprises three sections; an outer ear 42, middle ear 44, and inner ear 46. The outer ear 42 includes an auricle 48, earlobe 50, and auditory canal 52. The middle ear 44 includes an ear drum 54 and a tympanic cavity 56. The auditory canal 52 of the outer ear 42 ends at the ear drum (tympanic membrane) 54. Within the tympanic cavity 56 is a malleus bone 58, incus bone 60, and stapes bone 62. The ear drum 54 is in communication with the malleus 58, the malleus 58 is in communication with the incus 60, and the incus is in communication with the stapes 62, with the incus 60 being positioned between the malleus 58 and the stapes 62. The inner ear 46 includes semicircular ducts 64, including a superior semicircular canal 65, a cochlea 66, and an auditory tube 68. A portion of lateral skull base 67 (i.e., a portion of the temporal bone 30) is superior to the superior semicircular canal 65. The stapes 62 of the middle ear 44 is in communication with the cochlea 66 and the auditory tube 68 is in communication with the tympanic cavity 56. FIG. 2 also shows the tegmen tympani 32 of the temporal bone 30, which separates a cranial cavity 70 from the tympanic cavity 56, and the tegmen mastoideum 33 of the temporal bone 30, which separates the cranial cavity 70 from mastoid cells 71.

Figure 3:
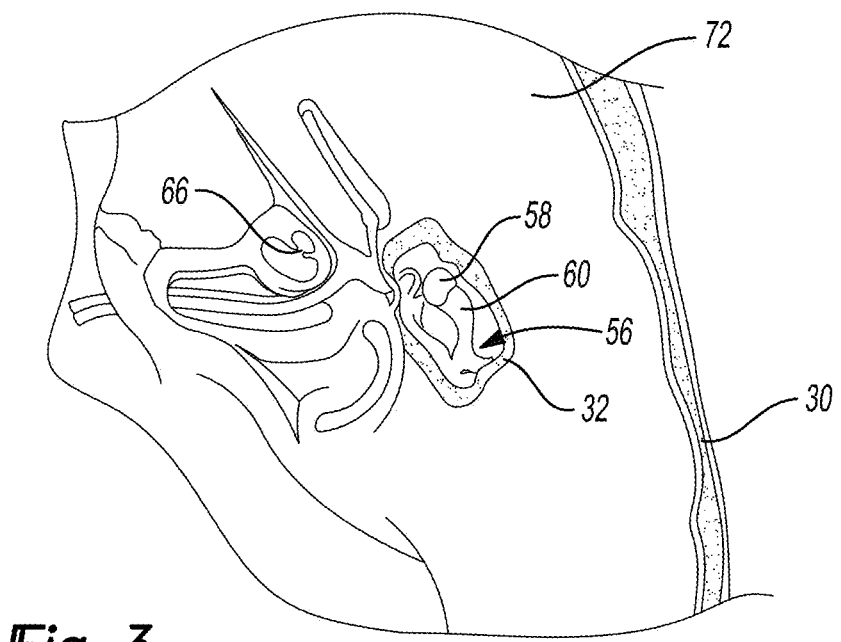
FIG. 3 is an illustration of a superior surface of a temporal bone.

FIG. 3 is an illustration of a superior surface 72 of the temporal bone 30. In this illustration, portions of the temporal bone 30 are removed to show the anatomy immediately inferior of the temporal bone 30. For instance, a portion of the temporal bone 30 that includes the tegmen tympani 32 is removed, which exposes the malleus 58 and incus 60 within the tympanic cavity 56. A portion of the temporal bone 30 is also removed that exposes the cochlea 66.

Defects of the tegmen tympani and/or tegmen mastoideum often occur without obvious etiology and may be congenital or a result of intracranial hypertension. Collectively, the tegmen tympani and tegmen mastoideum are referred to herein as the "tegmen." Accordingly, defects of the tegmen tympani, defects of the tegmen mastoideum, and defects that span the tegmen tympani and the tegmen mastoideum, are referred to herein as "tegmen defects" or "defects of the tegmen." Some subjects with tegmen defects are asymptomatic. Other subjects with defects in the tegmen have unpleasant side effects. These subjects may present with otologic or vestibular complaints, such as decreased hearing, pulsatile tinnitus (hearing of sound when no external sound is present), or tullio phenomenon (sound-induced vertigo, dizziness, nausea, or eye movement (nystagmus)). Other symptoms includes dizziness (including imbalance, lightheadedness, and vertigo), and cerebrospinal fluid (CSF) leaks, which can present with persistent rhinorrhea and subject patients to an increased risk of meningitis. Additionally, tegmen defects may result in temporal encephaloceles (protrusions of the temporal lobe of the brain through openings in the skull), meningitis, and CSF leaks. Examples of CSF leaks include persistent middle ear effusions (MEEs), which refers to fluid build-up in the middle ear. Non-limiting examples of MEEs include otitis media with effusion (OME), also referred to as serous otitis media, and otorrhea (ear discharge) or rhinorrhea (nasal discharge).

FIG. 4 shows an exemplary tegmen defect. Including other features described in regard to FIG. 2, FIG. 4 shows the temporal bone 30 with a defect in the tegmen 32, 33, manifested as a hole 74. Here, as an example of an encephalocele, a temporal lobe 76 of a brain 78 has extended from the cranial cavity 70, through the hole 74 in the tegmen 32, 33 and into the tympanic cavity 56. In this example, the temporal lobe 76 of the brain 78 interferes with the malleus 58 and incus 60, which may lead to at least one of symptoms described above.

As discussed above, current methods for repairing tegmen defects are challenging and not completely effective. Moreover, all subjects in need of a tegmen repair have individual and distinct anatomies because of variability in floors of the lateral skull base. Therefore, a single implant will fit differently in different patients. According, in various aspects, the present disclosure provides methods for manufacturing custom prosthetic tegmen plates for implanting in a subject in need thereof. Methods for treating tegmen defects with the custom prosthetic tegmen plates are also presented. Although the methods are particularly useful for treating human subjects or human patients with tegmen defects, it is understood that the methods can be adopted for other non-human mammals.

FIG. 5 shows a method 100 for manufacturing a prosthetic tegmen plate for implanting in a subject in need thereof. The prosthetic tegmen plate is custom made to fit on a surface of a particular subject's temporal bone, such that the prosthetic tegmen plate covers a defect in the subject's tegmen. The subject can be any human or non-human mammal with a tegmen defect. In addition, a subject may have multiple tegmen defects in a single temporal bone. Although some subjects having tegmen defects are asymptomatic, many subjects present with at least one of the symptoms described above.

In block 102, the method 100 comprises preoperatively imaging at least a portion of the subject's temporal bone to provide images that include the subject's tegmen. The images of the subject's tegmen show the defect that will be treated. In certain embodiments, the defect is a hole and/or fissure or a plurality of holes and/or fissures that allow the subject's cranial cavity to communicate with the subject's tympanic cavity and/or mastoid. Accordingly, the subject may have a plurality of defects on the tegmen. Imaging at least a portion of the subject's temporal bone comprises generating images of the subject's temporal bone, including the tegmen and defect associate therewith, by magnetic resonance imaging (MRI), computed tomography (CT), positron emission tomography (PET), ultrasound, X-ray, or a combination thereof. In various aspects, the preoperative image is a CT scan having a slice thickness of from greater than or equal to about 0.25 mm to less than or equal to about 1 mm, or from greater than or equal to about 0.5 mm to less than or equal to about 0.75 mm, such as a thickness of about 0.25 mm, about 0.3 mm, about 0.35 mm, about 0.4 mm, about 0.45 mm, about 0.5 mm, about 0.55 mm, about 0.6 mm, about 0.625 mm, about 0.65 mm, about 0.675 mm, about 0.7 mm, about 0.75 mm, about 0.8 mm, about 0.9 mm, or about 1 mm. FIG. 6A shows a CT scan of a subject's middle cranial fossa that includes a temporal bone 112 displayed in a first orientation, FIG. 6B shows the CT scan of the temporal bone 112 in a second orientation, and FIG. 6C shows the CT scan of the temporal bone 112 in a third orientation.

With renewed reference to FIG. 5, in block 104 the method 100 comprises generating or a first three dimensional (3D) model of at least a portion of the subject's temporal bone comprising the tegmen, such as a 3D computer rendering of the temporal bone or portion thereof. More particularly, the 3D model is generated from the preoperative images of the subject's temporal bone that include the subject's tegmen and associated tegmen defect. Other associated defects, such as a dehiscence of a superior semicircular canal (also known as superior semicircular canal dehiscence (SSCD) that occurs when a defect in the lateral skull base causes the superior semicircular canal to protrude through the defect) may also be included in the first 3D model. Generating the 3D model of the temporal bone also includes segmenting the preoperative image of the temporal bone using suitable software to zoom in on and capture the tegmen in detail. Therefore, a 3D object is created with high resolution and details of the tegmen's contour are not lost. A surface of the 3D model of the temporal bone is then smoothed using the software. Generating the 3D model of the temporal bone, including the segmenting and the smoothing, can be performed with any program and/or software, such as image processing software, known in the art for generating 3D models from scan data or images. Non-limiting examples of software that is suitable for generating 3D models include MIMICS® (Materialise Interactive Medical Image Control System) image processing software (Materialse NV, Belgium) and ITK_Snap image processing software (University of Pennsylvania and University of Utah). Accordingly, the method 100 comprises creating a first 3D model of the tegmen defect from preoperative images of the subject's temporal bone.

Figure 6B:
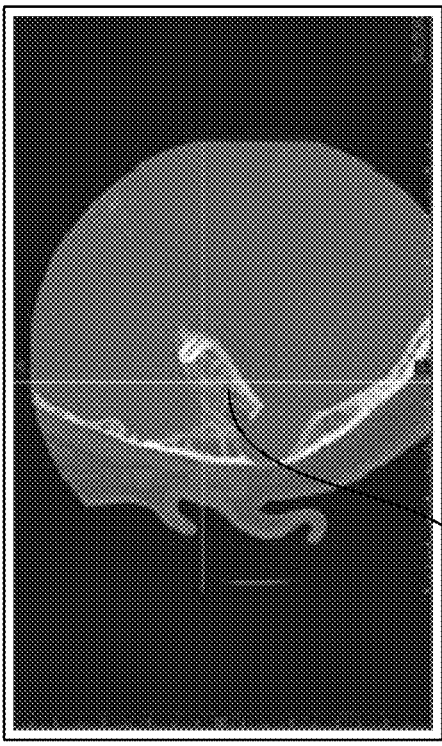
FIG. 6B shows a CT scan of a subject's middle cranial fossa that includes a temporal bone displayed in a second orientation.
Figure 6D:
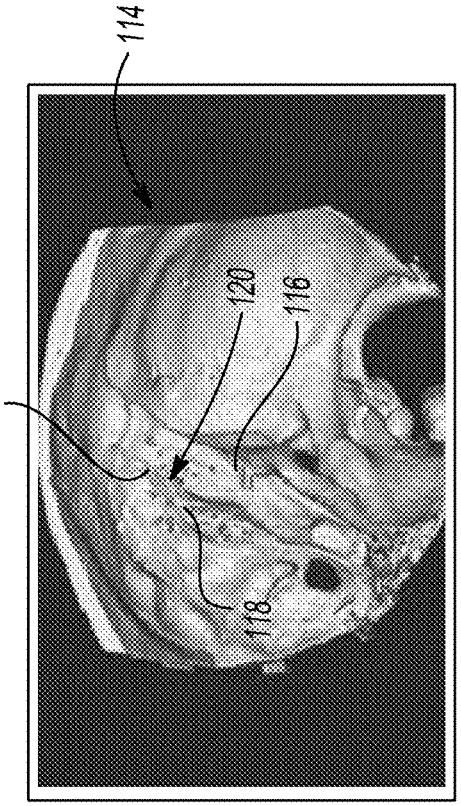
FIG. 6D shows a 3D model generated from the CT scan depicted in FIGS. 6A-6C.
Figure 6A:
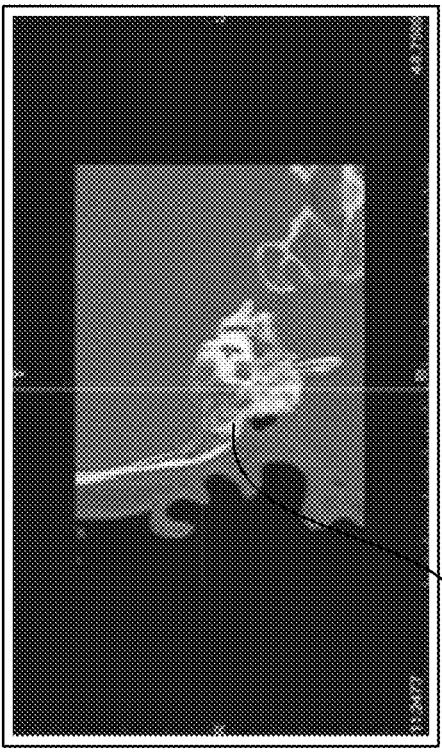
FIG. 6A shows a CT scan of a subject's middle cranial fossa that includes a temporal bone displayed in a first orientation.
Figure 6C:
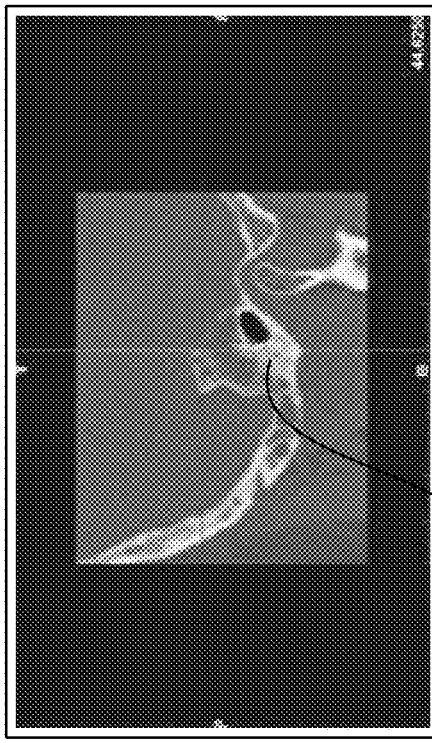
FIG. 6C shows a CT scan of a subject's middle cranial fossa that includes a temporal bone displayed in a third orientation.
Figure 7:
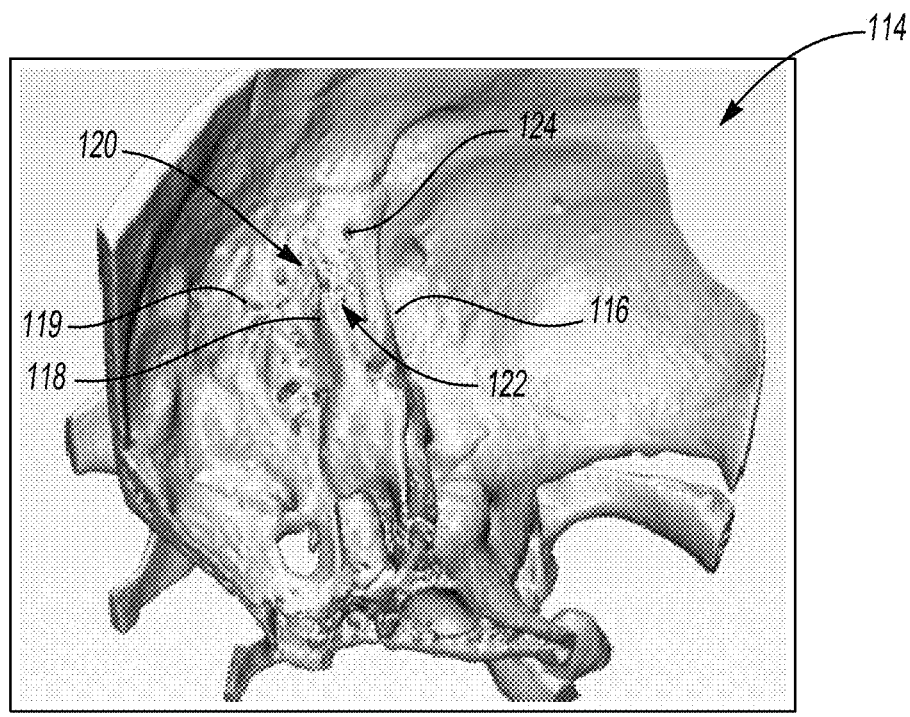
FIG. 7 shows another perspective of the 3D model shown in FIG. 6D.

FIG. 6D shows a high resolution 3D model 114 generated from the CT scan depicted in FIGS. 6A-6C. Although other programs and/or software may be used for generating 3D models from images, the 3D model 114 of FIG. 6D was generated from MIMICS® image processing software. The 3D model 114 includes the subject's temporal bone 116, tegmen tympani 118, tegmen mastoideum 119, and tegmen defect 120. Here, the tegmen defect 120 is manifested as a plurality of irregularly shaped holes. FIG. 7 provides another view of the high resolution 3D model 114 shown in FIG. 6D. Every subject has a unique anatomical geometry and contours on a superior surface of the temporal bone and tegmen. Therefore, every prosthetic tegmen plate manufactured by the present technology is unique to a particular subject. In FIG. 7, 3D contours 122 on a superior surface 124 of the subject's temporal bone 116 and tegmen 118, 119 are identified.

Referring back to FIG. 5, in block 106 the method comprises designing a second 3D model of a prosthetic tegmen plate, i.e., a model prosthetic tegmen plate. In particular, designing a 3D model of a prosthetic tegmen plate includes designing a 3D model of a prosthetic tegmen plate comprising a mating surface complimentary to at least a portion of the subject's temporal bone comprising the tegmen defect. The prosthetic tegmen plate in the 3D model covers the defect in the subject's tegmen, and when the subject has, for example, SSCD, the 3D model also covers a defect in the subject's superior semicircular canal. The 3D model of a prosthetic tegmen plate can be generated with the same program and/or software used to generate the first 3D model generated from the preoperative images or the first 3D model generated from the preoperative images can be imported into an additional program and/or software for designing the second 3D model of a prosthetic tegmen plate, such as, for example, 3-MATIC 3D modeling software by Materialise (Belgium). Accordingly, the method 100 comprises creating a second 3D model of the prosthetic tegmen plate complementary to at least apportion of the first 3D model.

In various aspects, creating a model tegmen plate includes isolating a defect portion of the 3D model of the temporal bone having the defect, and separating the defect portion from the 3D model of the temporal bone. Creating the model tegmen plate also includes repairing the defect in the defect portion with local smoothing to clean the defect and smooth the defect's contours as needed without altering the overall contour of the defect portion. By "without altering the overall contour of the defect portion" means that the overall contour of the defect portion is not substantially changed such that the model tegmen plate will still conformingly fit over the defect in the subject.

Creating the model tegmen plate then includes drawing a two dimensional smooth curve about and around the defect to outline a shape of the model tegmen plate and cutting a surface plane along the smooth curve having edges defined by the outline. The shape of the model tegmen plate has a size in two orthogonal directions of at least about 3×3 mm, at least about 4×4 mm, or at least about 5×5 mm. In some aspects, a central portion of the plane is elevated off the defect to a height of from greater than or equal to about 0.05 to less than or equal to about 1 mm, from greater than or equal to about 0.1 to less than or equal to about 0.4 mm, from greater than or equal to about 0.15 to less than or equal to about 0.35 mm, or from greater than or equal to about 0.2 to less than or equal to about 0.3 mm, such as a height of about 0.05 mm, about 0.1 mm, about 0.15 mm, about 0.2 mm, about 0.25 mm, about 0.3 mm, about 0.35 mm, about 0.4 mm, about 0.5 mm, about 0.6 mm, about 0.7 mm, about 0.8 mm, about 0.9 mm, or about 1.0 mm. When the central portion is elevated, the model tegmen plate has an unmodified portion that extends inward from the edges toward the central portion and having a length of at least about 2 mm, at least about 2.5 mm, at least about 3 mm, at least about 3.5 mm, or at least about 4 mm, such as a length of about 2 mm, about 2.5 mm, about 3 mm, about 3.5 mm, about 4 mm, about 4.5 mm, about 5 mm or longer. The unmodified portion ensures that at least the unmodified portion of the model tegmen plate will conformingly rest on the subject's temporal bone when the central portion is elevated. Accordingly, the unmodified portion includes at least one engagement surface.

Creating the model tegmen plate further includes offsetting the surface plane, i.e., the two dimensional outline, to generate a 3D construct or model tegmen plate having a thickness of at least about 0.5 mm, at least about 0.6 mm, at least about 0.7 mm, at least about 0.8 mm, at least about 0.9 mm, at least about 1.0 mm, at least about 1.1 mm, at least about 1.2 mm, at least about 1.3 mm, at least about 1.4 mm, or at least about 1.5 mm to generate a 3D construct. In various aspects, the model tegmen plate has a thickness of less than or equal to about 10 mm, less than or equal to about 8 mm, less than or equal to about 7 mm, less than or equal to about 6 mm, less than or equal to about 5 mm, less than or equal to about 4 mm, less than or equal to about 3 mm, less than or equal to about 2 mm, or less than or equal to about 1 mm. Creating the model tegmen plate then includes smooth the edges of the 3D construct to generate the model tegmen plate.

Figure 8A:
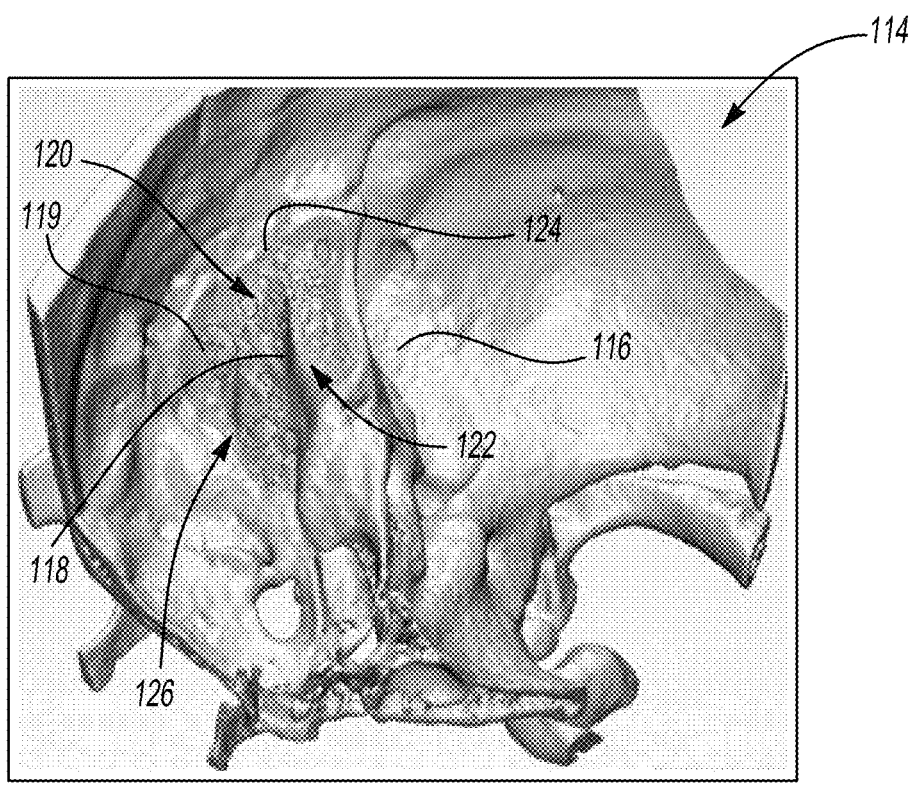
FIG. 8A shows the 3D model shown in FIG. 7 highlighting a region spanning a tegmen defect.
Figure 8B:
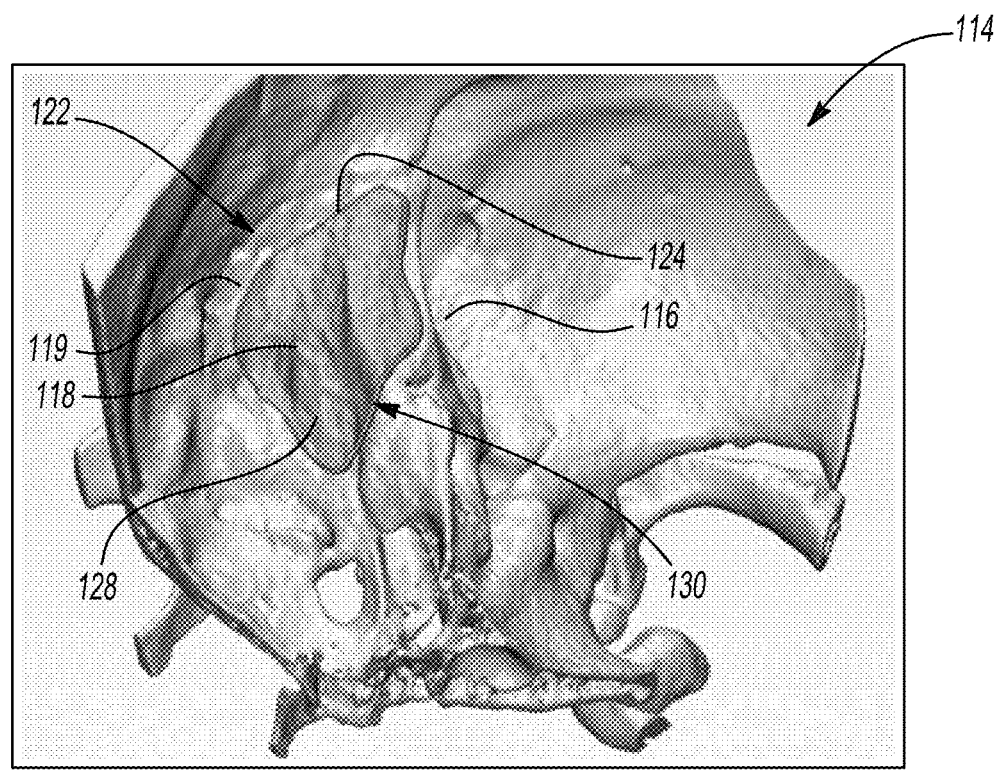
FIG. 8B shows a first perspective of a 3D model of a prosthetic tegmen plate disposed on the 3D model shown in FIG. 7.
Figure 8C:
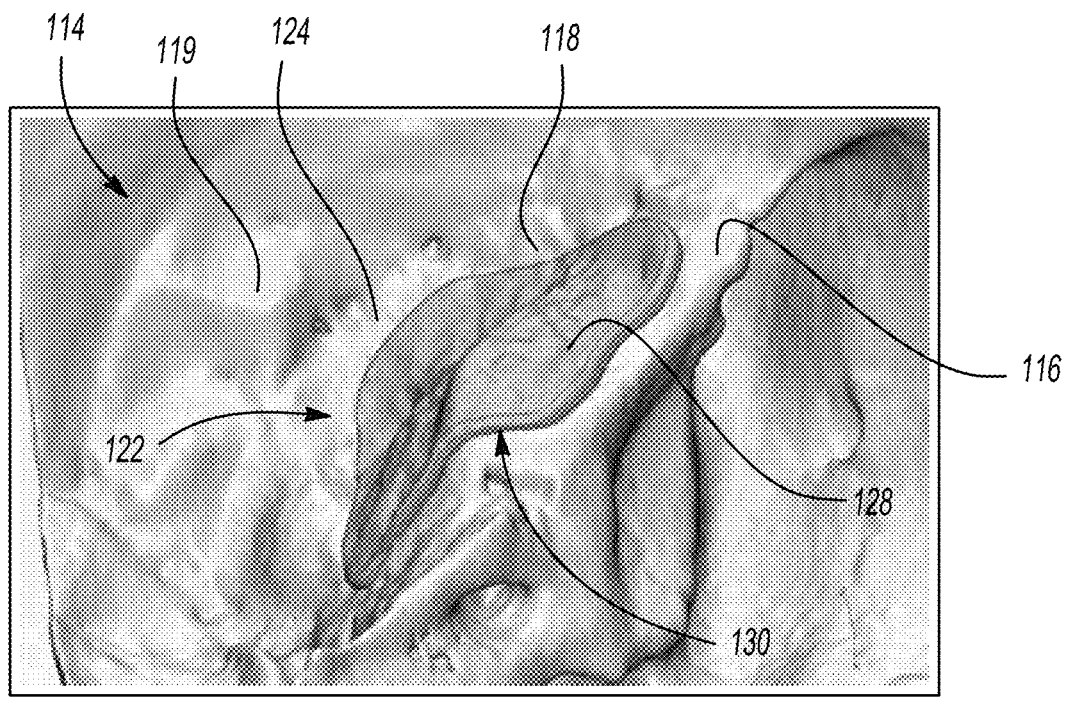
FIG. 8C shows a second perspective of a 3D model of a prosthetic tegmen plate disposed on the 3D model shown in FIG. 7.
Figure 9C:
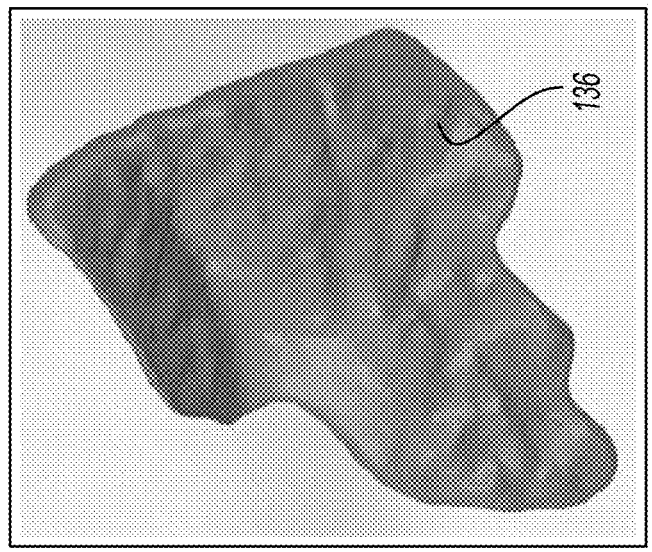
FIG. 9C shows a third 3D model of a prosthetic tegmen plate.
Figure 9B:
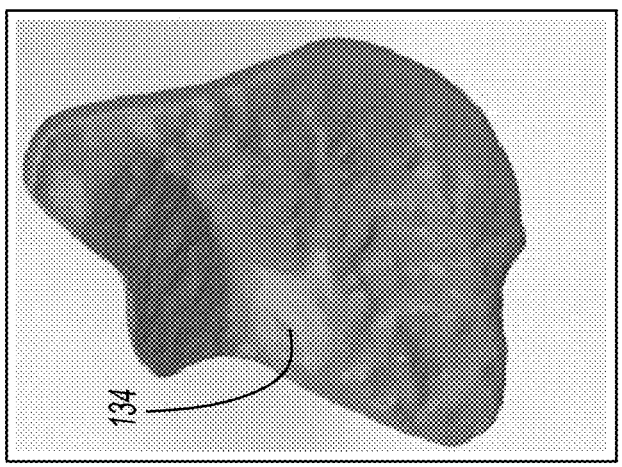
FIG. 9B shows a second 3D model of a prosthetic tegmen plate.
Figure 9A:
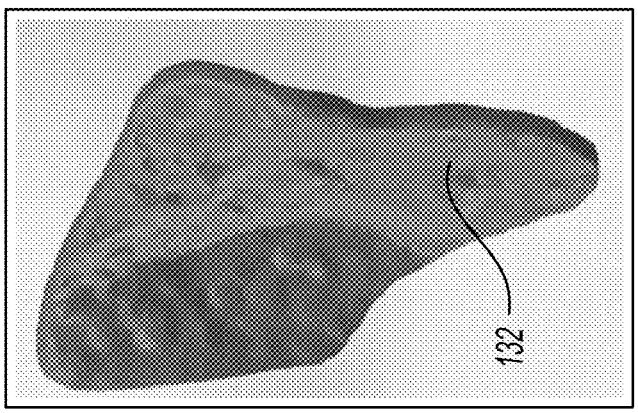
FIG. 9A shows a first 3D model of a prosthetic tegmen plate.

FIG. 8A shows the 3D model 114 of the temporal bone 116 and tegmen 118, 119. A region 126 of the tegmen 118, 119 spanning the defect 120 is highlighted in the figure. The region 126 is a surface of the temporal bone 116 and tegmen 118, 119 that will be covered by a prosthetic tegmen implant. FIGS. 8B and 8C show perspective views of a 3D model of a prosthetic tegmen plate 128 that is disposed on the region 126 of the tegmen 118, 119 spanning the defect 120 shown in FIG. 8A. The 3D model of a prosthetic tegmen plate 128 includes a mating surface 130 that is a negative of a corresponding surface of the subject's temporal bone 116 and tegmen 118, 119 identified as the region 126 in FIG. 8A. In other words, the mating surface 130 is a negative of the contours 122 on the superior surface 124 of the subject's temporal bone 116 and tegmen 118, 119 in the region 126 spanning the defect 120. FIG. 9A shows a perspective view of a 3D model of a prosthetic tegmen plate 132 that is specific to a second subject's temporal bone and tegmen, FIG. 9B shows a perspective view of a 3D model of a prosthetic tegmen plate 134 that is specific to a second subject's temporal bone and tegmen, and FIG. 9C shows a perspective view of a 3D model of a prosthetic tegmen plate 136 that is specific to a second subject's temporal bone and tegmen.

Referring back to FIG. 5, in block 108 the method 100 optionally further comprises importing the 3D model into suitable software for generating a prosthetic tegmen plate by additive manufacturing. When a prosthetic tegmen plate cannot be generated by additive manufacturing by the program and/or software used to generate the 3D model, the 3D model is imported into any suitable CAD program and/or software.

In block 110, the method 100 comprises generating the prosthetic tegmen plate that includes a mating surface that substantially conforms to a corresponding surface of the subject's temporal bone and tegmen. By "substantially conforms," it is meant that the mating surface is three-dimensionally contoured to match a corresponding surface, e.g., a superior surface, of the subject's temporal bone and tegmen that includes the defect, while permitting some amount of localized regional variation or deviation, so that the mating surface of the prosthetic tegmen plate nestingly mates to or rests against a corresponding surface of the subject's temporal bone in only a single orientation. In certain aspects, the amount of deviation may be a surface area of less than or equal to about 10%, optionally less than or equal to about 5%, optionally less than or equal to about 1%, optionally less than or equal to about 0.5%, optionally less than or equal to about 0.5%, and in certain aspects, optionally less than or equal to about 0.1%. In various aspects, the prosthetic tegmen plate has an elevated central portion and the mating surface includes an unmodified portion of the prosthetic tegmen plate that extends inward from the edges toward the central portion. The prosthetic tegmen plate includes the characteristics and parameters provided by the model prosthetic tegmen plate, such as size, thickness, etc.

Accordingly, the prosthetic tegmen plate is custom made for the specific subject. Generating a prosthetic tegmen plate comprises generating a prosthetic tegmen plate from the second 3D model of a prosthetic tegmen plate by additive manufacturing with a biocompatible material. Therefore, in various embodiments, the method 100 includes additive manufacturing the prosthetic tegmen plate from the second 3D model, wherein the mating surface of the prosthetic tegmen plate is complimentary to at least a portion of the subject's temporal bone comprising the tegmen based on the first 3D model. Accordingly, The prosthetic tegmen is generated with a thickness of less than or equal to about 10 mm, less than or equal to about 8 mm, less than or equal to about 7 mm, less than or equal to about 6 mm, less than or equal to about 5 mm, less than or equal to about 4 mm, less than or equal to about 3 mm, less than or equal to about 2 mm, or less than or equal to about 1 mm. In certain embodiments, the prosthetic tegmen plate is generated with a thickness of from about 1 mm to about 10 mm.

Additive manufacturing is a process by which a solid three-dimensional structure is built layer-by-layer, typically via a printing deposition process or where energy or heat is selectively applied to powder starting materials to solidify, fuse, or sinter and create a layer of solid material. Additive manufacturing is often referred to synonymously with three-dimensional printing ("3D printing"). Either polymers or metals may be used to create solid structures via additive manufacturing. Non-limiting examples of additive manufacturing processes include fused deposition modeling and selective laser sintering with polymers, such as thermosets and thermoplastics; stereolithography, continuous liquid interface production technology, or other technologies that rely on UV curable polymers; fused deposition modeling with composite polymers; direct metal laser sintering, electron beam direct metal melting systems, blown powder directed energy deposition, wire-fed directed energy deposition, and liquid metal 3D printing system with "Magnet-Jet" technology with metals, such as aluminum alloys, titanium alloys, and steel alloys. Moreover, a plurality of materials may be deposited at different locations of an object being built by a single machine.

By "biocompatible," it is meant that a material or combination of materials can be in contact with cells, tissue in vitro or in vivo, or used with a subject (such as mammals or other organisms) and has acceptable toxicological properties for contact and/or beneficial use with such cells, tissue, and/or animals. For instance, a biocompatible material may be one that is suitable for administration in a subject without adverse consequences, for example, without substantial toxicity or acute or chronic inflammatory response and/or acute rejection of the material by the immune system, for instance, via a T-cell response. It will be recognized, of course, that "biocompatibility" is a relative term, and some degree of inflammatory and/or immune response is to be expected even for materials that are highly compatible with living tissue. However, non-biocompatible materials are typically those materials that are highly toxic, inflammatory and/or are acutely rejected by the immune system, e.g., a non-biocompatible material implanted into a subject may provoke an immune response in the subject that is severe enough such that the rejection of the material by the immune system cannot be adequately controlled, in some cases even with the use of immunosuppressant drugs, and often can be of a degree such that the material must be removed from the subject. In certain aspects, biocompatible materials are those that are approved for use in humans by an appropriate regulatory agency, such as the Federal Drug Administration (FDA) in the United States; the European Commission (EC)/European Medicines Agency (EMEA) in Europe; or Health Products and Food Branch (HPFB) in Canada.

Generating a prosthetic tegmen plate comprises generating a prosthetic tegmen plate composed of a biocompatible material, such as, for example, a polymer, ceramic, metal, or combination thereof. In various embodiments, the biocompatible material comprises a supplemental component as described further below. The biocompatible material can be a non-bioresorbable polymer or a bioresorbable in certain embodiments.

By "bioresorbable," in certain aspects, the biocompatible material dissolves or disintegrates at different rates in vivo. Dissolving refers to physical disintegration, erosion, disruption and/or dissolution of a material and may include the resorption or assimilation of a material by a living organism. The polymeric material forming the nanoparticle may dissolve or disintegrate at different rates or have different solubility (e.g., aqueous solubility) that impacts the rate of dissolution. The materials can dissolve or erode upon exposure to a solvent comprising a high concentration of water, such as saliva, serum, growth or culture media, blood, or bodily fluids. Disintegration may also include the material breaking into small pieces, which may collectively form a colloid or gel.

By "non-bioresorbable," in certain aspects, the biocompatible material does not dissolve or disintegrate in vivo. Non-resorbable biocompatible materials do not dissolve or erode upon exposure to a solvent comprising a high concentration of water, such as saliva, serum, growth or culture media, blood, or bodily fluids. Rather, a non-bioresorbable biocompatible material remains substantially intact for the lifetime of a living organism into which it is implanted, i.e., is permanent. By "substantially intact" it is meant that the non-bioresorbable biocompatible material does not dissolve or disintegrate in vivo, for example, only a small portion of the bioresorbable biocompatible material dissolves or disintegrates at less than or equal to about 1.0% by weight, optionally less than or equal to about 0.5% by weight, optionally less than or equal to about 0.1%, and in certain preferred aspects, 0% by weight of the non-bioresorbable biocompatible material.

Non-limiting examples of suitable non-bioresorbable polymers include polyaryl ether ketone (PAEK), poly(methyl acrylate) (PMA), poly(methyl methacrylate) (PMMA), polyetherimide (PEI), polysulfone, polyphenolsulfone, copolymers thereof, and combinations thereof. In some embodiments, the non-bioresorbable material is a PAEK, such as polyetherketone (PEK), polyether ketone ketone (PEKK), polyether ether ketone (PEEK), polyether ether ketone ketone (PEEKK), polyether ketone ether ketone ketone (PEKEKK), copolymers thereof and combinations thereof. In some embodiments, the prosthetic tegmen plate is generated by 3D printing with PEKK. Metals are also non-bioresorbable. Non-limiting examples of suitable metals include titanium, steel, and stainless steel. Manufacturing a prosthetic tegmen plate from non-bioresorbable materials results in a prosthetic tegmen plate that is permanent.

Non-limiting examples of suitable bioresorbable polymers include poly lactic acid (PLA), poly glycolic acid (PGA), poly lactic co-glycolic acid (PLGA), polyhydroxybutyrate (PHB), polyhydroxyvalerate (PHV), poly(desaminotyrosyl-tyrosine ethyl carbonate) (poly(DTE-carbonate)), polycaprolactone, polyanhydrides, polyorthoesters, copolymers thereof, and combinations thereof. In other embodiments, the polymer is a polysaccharide selected from the group consisting of starch, alginate, hyaluronic acid, and combinations thereof or a protein selected from the group consisting of collagen, fibrin, silk, and combinations thereof.

In some aspects, the method for manufacturing a prosthetic tegmen plate further comprises contacting the prosthetic tegmen plate with a supplemental component or material. Contacting the prosthetic tegmen plate with a supplemental component incorporates the supplemental component into the biocompatible material of the prosthetic tegmen plate. Therefore, in certain aspects, the prosthetic tegmen plate comprises at least one supplemental component. In some embodiments, a prosthetic tegmen plate manufactured from a bioresorbable material is contacted with the supplemental component. The supplemental component can promote bone ingrowth at a site of implantation, prevent or decrease inflammation associated with the defect and/or with a surgical procedure performed to implant the prosthetic tegmen plate, and/or prevent or decrease infection. Blood fractions, such as platelet poor plasma or platelet-rich plasma, which are rich in growth factors and anti-inflammatory components, can also be contacted with the prosthetic tegmen plate. Accordingly, the supplemental component can be at least one growth factor, a suspension of at least one type of cell, at least one anti-inflammatory agent, at least one antimicrobial agent, a blood fraction, or a combination thereof.

Non-limiting examples of growth factors that can be contacted with the prosthetic tegmen plate include platelet-derived growth factor-AB (PDGF-AB), platelet-derived growth factor-BB (PDGF-BB), insulin-like growth factor-I (IGF-I), transforming growth factor-β1 (TGF-β1), hepatocyte growth factor (HGF), vascular endothelial growth factor (VEGF), epidermal growth factor (EGF), and combinations thereof.

Non-limiting examples of cells that can be contacted with the prosthetic tegmen plate include stromal cells, mesenchymal stem cells and a combination thereof.

Non-limiting examples of anti-inflammatory agents include, cytokines, such as interleukin-1 receptor antagonist (IL-1ra), interleukin-18 receptor antagonist (IL-18ra), interleukin-4 (IL-4), interleukin-6 (IL-6), interleukin-10 (IL-10), interleukin-11 (IL-11), interleukin-13 (IL-13), interleukin-16 (IL-16), and interferon-α (INFα); cytokine receptors, such as soluble tumor necrosis factor-receptor I (sTNF-RI), soluble tumor necrosis factor-receptor II (sTNF-RII), soluble interleukin-1 receptor II (sIL-1RII); and combinations thereof.

Non-limiting examples of antimicrobial agents include antibiotics, such as rifamycins, fosfobycin, fusidic acid, glycylcyclines, aminoglycosides, quinolones, glycopeptides, bismuth thiols, sulfonamides, trimethoprim, macrolides, oxazolidinones, β-lactams, lincosamides, chloramphenicol, gramicidins, polymyxins, lipodepsipeptides, bacitracins, tetracyclines, penicillin, ampicillin, cefazolin, clindamycin, erythromycins, levofloxacin, and vancomycin; antifungal agents; antiviral agents; and combinations thereof.

Contacting the prosthetic tegmen plate with a supplemental component can be performed as part of the method for manufacturing the prosthetic tegmen plate or it can be performed by a medical professional prior to surgical implantation.

Figure 10A:
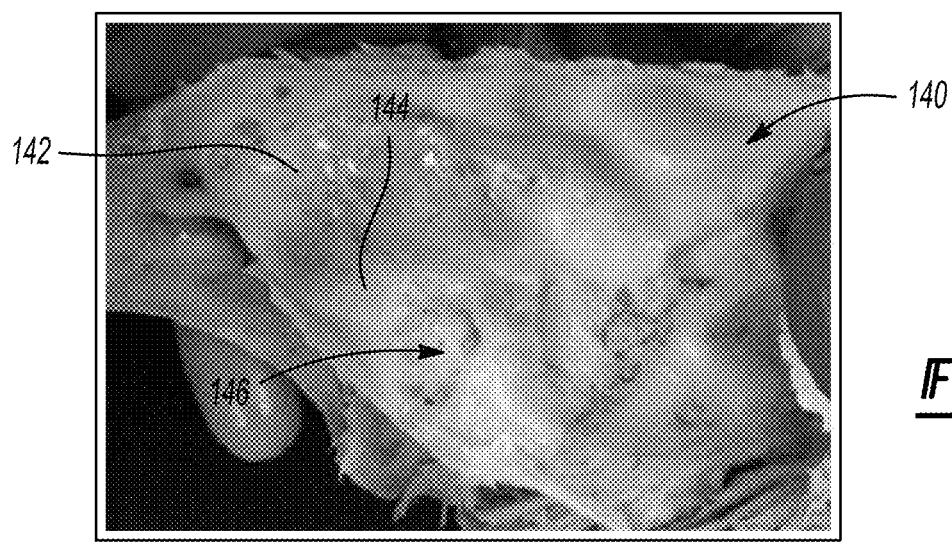
FIG. 10A shows a resected section of a cranial base from a first cadaver that includes a temporal bone and tegmen.
Figure 10B:
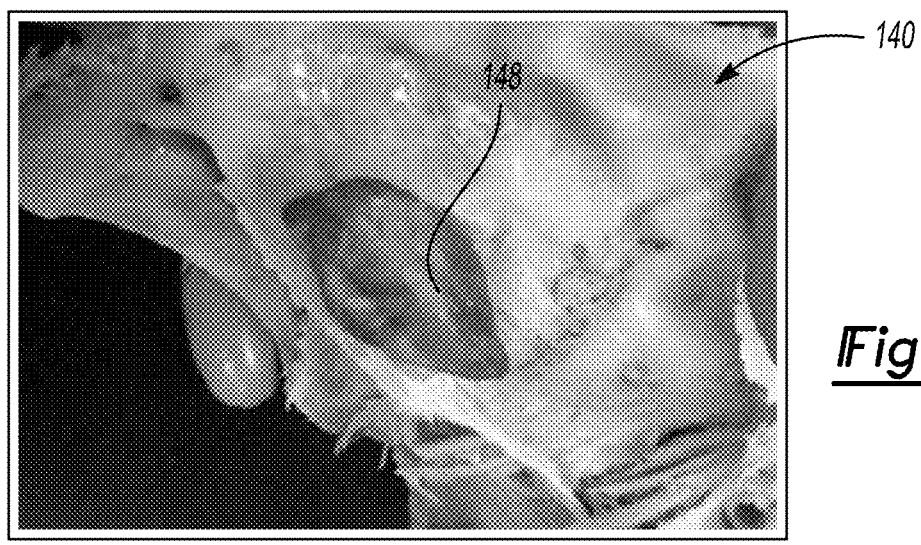
FIG. 10B shows a first perspective of a prosthetic tegmen plate disposed on the cranial base, wherein the prosthetic tegmen plate was manufactured by the method of FIG. 5.
Figure 10C:
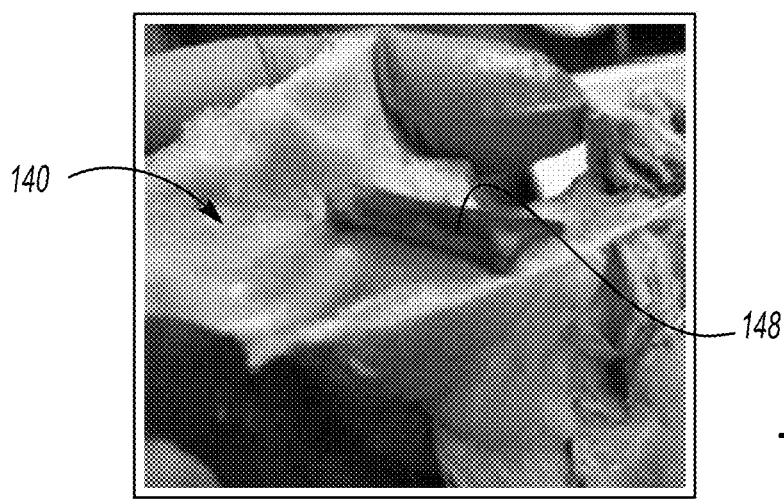
FIG. 10C shows a second perspective of a prosthetic tegmen plate disposed on the cranial base, wherein the prosthetic tegmen plate was manufactured by the method of FIG. 5.

FIG. 10A shows a resected section of a cranial base 140 from a cadaver that includes a temporal bone 142 and tegmen 144. A defect 146 is present in the tegmen 144. As shown in FIGS. 10B and 10C, the method 100 of FIG. 5 was performed to generate a prosthetic tegmen plate 148 from PLA. The prosthetic tegmen plate 148 has a surface that nestingly mates and conforms to a corresponding surface of the temporal bone 142. Because PLA is a bioresorbable biocompatible material, the prosthetic tegmen plate 148 may be contacted with a supplemental component as described above.

Figure 11A:
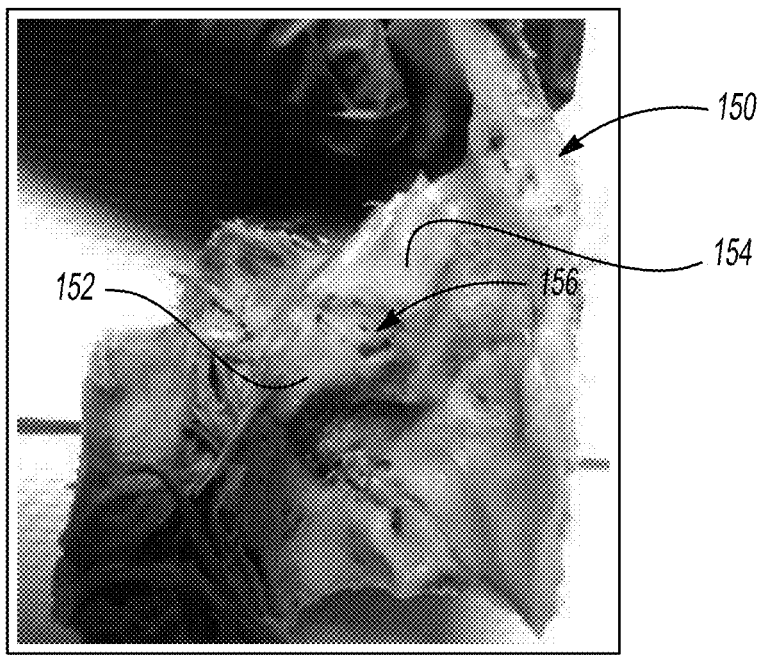
FIG. 11A shows a resected section of a cranial base from a second cadaver that includes a temporal bone and tegmen.
Figure 11B:
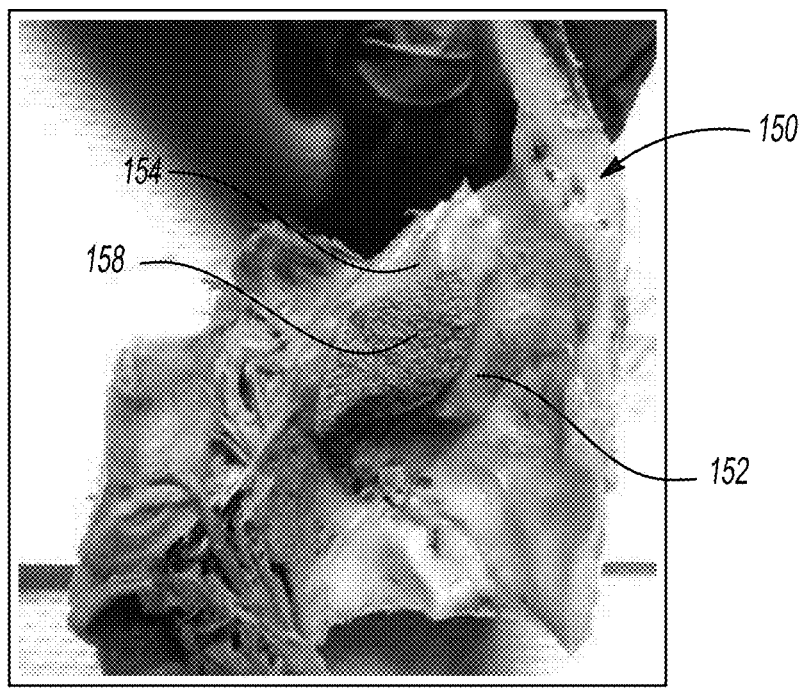
FIG. 11B shows a perspective of a prosthetic tegmen plate disposed on the cranial base, wherein the prosthetic tegmen plate was manufactured by the method of FIG. 5.

FIG. 11A shows a resected section of a cranial base 150 from a second cadaver that includes a temporal bone 152 and tegmen 154. A defect 156 is present in the tegmen 154. As shown in FIG. 11B, the method 100 of FIG. 5 was performed to generate a prosthetic tegmen plate 158 from PEKK. The prosthetic tegmen plate 158 has a surface that nestingly mates and conforms to a corresponding surface of the temporal bone 152.

The present technology also provides a prosthetic tegmen plate made by the method 100 of FIG. 5. The prosthetic tegmen plate comprises a body formed by additive manufacturing comprising a biocompatible material. The body defines at least one engagement surface that substantially conforms to a region of a corresponding surface of a subject's temporal bone comprising a tegmen defect. The prosthetic tegmen plate is configured to cover the tegmen defect. The prosthetic tegmen plate has any combination of characteristics described above in regard to the method 100 of manufacturing a prosthetic tegmen plate. Accordingly, the prosthetic tegmen plate has the thickness described above and is composed of at least one of the biocompatible materials described in regard to the method 100, which includes a supplemental component in certain aspects. In certain aspects, the prosthetic tegmen plate includes an elevated portion and an unmodified portion comprising the engagement surface as described above. The prosthetic tegmen plate nestingly mates to a corresponding surface of a subject's temporal bone in only a single orientation, such that it covers a defect in the subject's tegmen.

Additionally, the present technology provides a method of implanting a prosthetic tegmen plate in a subject having a tegmen defect using a prosthetic tegmen plate made by the method 100 of FIG. 5. The method repairs, or alleviates the symptoms associated with, the tegmen defect in the subject. The defect in the temporal plate can be associated with any of the symptoms described herein. The method comprises a pereioperative protocol that includes non-limiting details about inclusion criteria, exclusion criteria, materials handling, pre-operative evaluation, surgical approach, perioperative medications and treatments, intra-operative monitoring, post-operative monitoring, post-operative imaging, post-operative audiogram, and metrics.

For example, inclusion criteria include: (1) adult patients (great than or equal to about 18 years of age), and (2) radiographic presence of tegmen tympani and/or tegmen mastoideum defects on imaging, such as, for example, CT imaging.

Exclusion criteria include: (acute inflammatory changes in the temporal bone (e.g., recent infection/meningitis or cholesteatoma erosion through the skull base, and (2) history of radiation to the middle fossa floor. Notwithstanding, presence of SSCD does not exclude a patient from undergoing the method and presence or absence of a CSF leak does not exclude a patient from undergoing the method. There is no upper limit for age criteria; however, it is understood that individual medical department's age selection criteria for patients undergoing middle fossa craniotomy can be followed.

Materials and handling criteria provide that prosthetic tegmen plates and temporal bone models can be autoclaved according to individual institutional standards and those provided by the Office of Personnel Management.

Pre-operative evaluation includes: (1) high0resolution scanning, such as a high-resolution CT temporal bone scan with imaging slices of less than or equal to about 1 mm thick, (2) pre-operative audiogram within 6 months of surgery, and (3) neurophysiologic testing to confirm SSCD (if indicated).

The surgical approach includes a middle fossa craniotomy, which is an exemplary method of exposure of the tegmen defect. The affected region of the middle fossa floor is fully visualized with the dura gently elevated. If the patient has SSCD, then the superior canal can be plugged as per surgeon preference. Antibiotic irrigation can be performed before introducing the prosthetic tegmen plate into an operative field. The prosthetic tegmen plate may be placed with a smooth side of the plate facing the dura. A small amount of bone cement (e.g., hydroxyl apatite or similar material) is placed on the periphery of the plate as a method of fixation to secure its position onto the middle fossa floor and prevent migration. Bone cement is then given adequate time to dry. Temporalis fascia or synthetic dural replacement (e.g.: DURAGEN® dural regeneration matrix from Integra Life Sciences (Plainsboro, N.J.)) may be placed over the prosthetic tegmen plate and/or bone cement so that an additional layer of lining between dura and the plate may be provided. A bone flap is returned to its anatomic position and the wound is closed.

Perioperative medications and treatments include antibiotics, steroids, reducing intracranial pressure, and lumbar drain. In regard to antibiotics, for non-allergic patients, IV cefuroxime is a non-limiting example of a suitable perioperative antibiotic. Antibiotics are given per standard protocol pre-incision and dosed accordingly intra-operatively. Patients may remain on intravenous (IV) antibiotics while in the immediate post-operative period and transitioned to an oral equivalent as an outpatient for a total of, for example, about 7 days of antibiotic duration. Allergic patients can be treated in a similar fashion with an appropriate antibiotic for middle fossa surgery. Discretionary steroids can be used for standard middle fossa surgery and afterwards. In regard to reducing intracranial pressure, a patient may receive from greater than or equal to about 25 gm to less than or equal to about 50 gm of mannitol, intra-operatively, prior to significant dural manipulation (assuming no contraindication). Post-operative mannitol may be administered. Hyperventilation for reduction of end-tidal $CO_2$ can be performed at the surgeon's discretion. These procedures may be followed by a lumbar drain based on the surgeon's discretion and standard practice for middle fossa surgery.

Intra-operative monitoring may include facial nerve monitoring. If SSCD will be addressed, the surgeon may ask for intra-op auditory brainstem response (ABR) and electrocochleography (ECOG) testing (based on surgeon preference).

Post-operative monitoring includes admission to an intensive care unit and continued hospitalization as per the surgeon's discretion.

Post-operative imaging can include a scan, such as, for example, a CT scan of the temporal bones without contrast within about the first six months post-operatively.

A post-operative audiogram can be performed at about six weeks post-operatively. Subsequent audiograms can be performed at the surgeon's discretion.

Metrics include: (1) total operative time, (2) duration of temporal lobe retraction, (3) radiographic resolution of tegmen defects after surgical repair (e.g., comparing pre and post op CT scans), (4) Resolution of CSF rhinorrhea or otorrhea (if present pre-operatively), such as a tip test performed at some point in the post op 30 day period, (5) pre- and post-operative audiogram data can be compared to assess for changes, (6) facial nerve function can be evaluated pre-operatively and post-operatively for any changes, and (7) standard complications associated with middle fossa surgery can be recorded (e.g., stroke, aphasia, intracranial hemorrhage, deep vein thrombosis (DVT), etc.).

The method, i.e., surgical approach, also comprises implanting a prosthetic tegmen plate in the subject so as to cover the tegmen defect. The prosthetic tegmen plate has a mating surface complementary to at least a portion of the subject's temporal bone comprising the tegmen defect. The prosthetic tegmen plate is generated from a 3D model created from preoperative images of the subject's temporal bone as described in regard to the method 100 of FIG. 5. The mating surface substantially conforms to a corresponding surface of the subject's temporal bone after the implanting. Because the prosthetic tegmen plate is custom made for the subject, the prosthetic tegmen plate nestingly mates and conforms to a corresponding surface of the subject's temporal bone in only a single orientation. In some embodiments, implanting the prosthetic tegmen plate does not include any anchoring or fastening of the prosthetic tegmen plate to the subject's temporal bone with hardware or adhesives. In other embodiments, implanting the prosthetic tegmen plate includes fastening the prosthetic tegmen plate to the subject's temporal bone with hardware or adhesives, such as, for example, a bone cement.

In various aspects, the method of implanting a prosthetic tegmen plate in the subject further comprises carving a window through a parietal bone of the subject; exposing the tegmen defect, such as by retracting a lobe of the subject's brain, and implanting or disposing the prosthetic tegmen plate on the subject's temporal bone, such that the prosthetic tegmen plate covers the subject's tegmen defect. The prosthetic tegmen plate has a surface that nestingly mates and conforms to a corresponding surface of the subject's temporal bone. In various embodiments, the method further comprises sealing the prosthetic tegmen implant with a layer of the subject's fascia. Because the prosthetic tegmen implant is sealed with the fascia, it is not necessary to fasten the prosthetic tegmen plate to the temporal bone with hardware or an adhesive. Nonetheless, a medical practitioner may choose to fasten the prosthetic tegmen plate to the temporal bone for added security.

In embodiments where the prosthetic tegmen implant is manufactured from a bioresorbable material, the method may also comprise contacting the prosthetic tegmen implant with at least one supplemental component as described above. For example, when the prosthetic tegmen implant is composed of a bioresorbable material and contacted with a suspension of mesenchymal stem cells and/or stromal cells, the mesenchymal and/or stromal cells will form bone to seal the defect as the prosthetic tegmen implant bioresorbs. Nonetheless, the prosthetic tegmen implant may be contacted with any combination of the supplemental components. Accordingly, in various embodiments, the prosthetic tegmen defect comprises any combination of supplemental components described herein.

In embodiments where the prosthetic tegmen implant is manufactured from a non-bioresorbable material, the method may also comprise contacting the prosthetic tegmen implant with at least one supplemental component as described above. However, because the prosthetic tegmen implant is not bioresorbable, contacting the prosthetic tegmen implant with a suspension of cells is not necessary.

Embodiments of the present technology are further illustrated through the following non-limiting examples.

Example 1

Figure 12C:
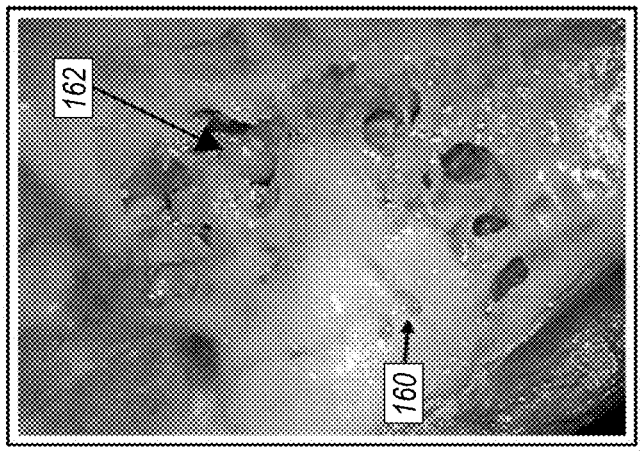
FIG. 12C shows a microscopic view of the tegmen defects present in the temporal bone shown in FIG. 12A, wherein the defects include a defect in the superior semicircular canal with a head of a malleus bone visible though the tegmen defects.
Figure 12B:
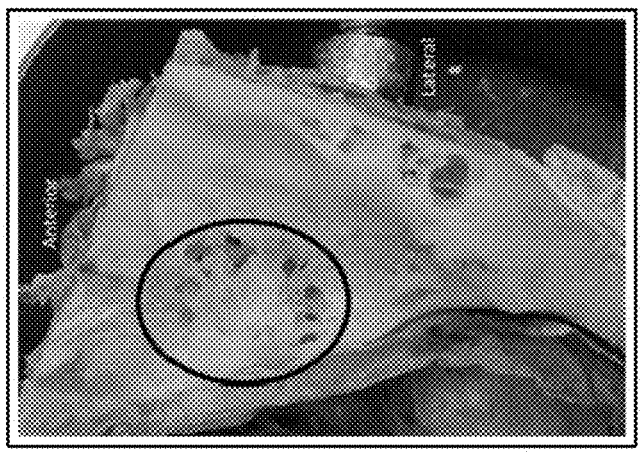
FIG. 12B shows the photograph of FIG. 12A, wherein the defects are shown within the circle.
Figure 12A:
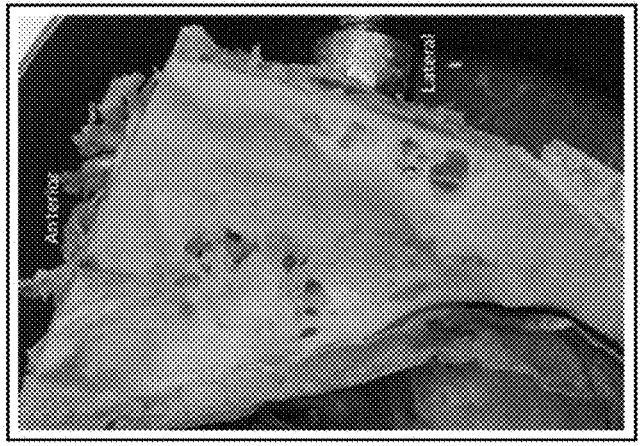
FIG. 12A is a photograph of a right cadaveric temporal bone with multiple tegmen defects viewed from cephalad.
Figure 13A:
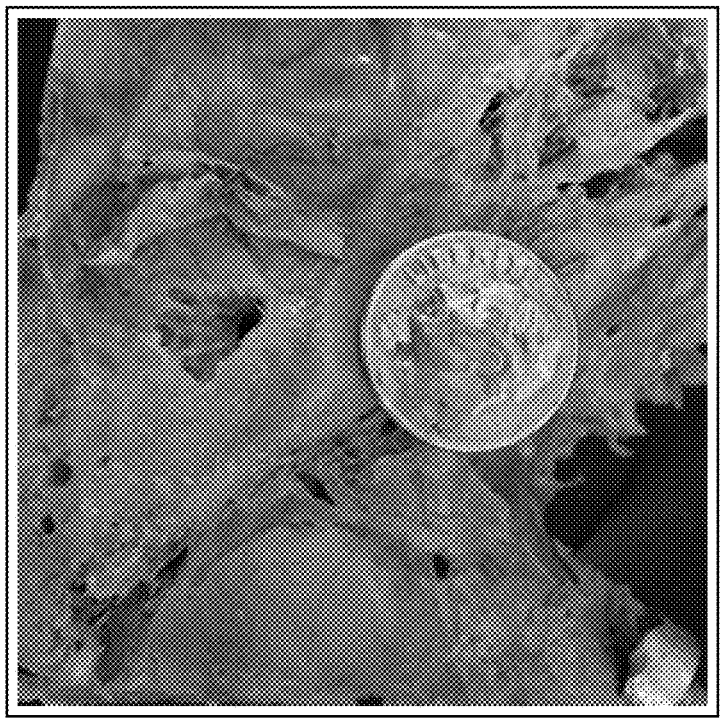
FIG. 13A is a photograph of a left cadaveric temporal bone with a large tegmen tympani defect shown from cephalad with a dime for size disposed thereon for reference.
Figure 13B:
FIG. 13B is a microscopic view of the tegmen defect shown in FIG. 13A.

Prosthetic tegmen implants are made using three separate cadaveric temporal bones that are formalin fixed. Using three separate temporal bones, various defects in the middle fossa (with or without superior semicircular canal dehiscence (SSCD)) are shown in FIGS. 12A, 12B, 12C, and FIGS. 13A and 13B. Multiple defects are created in two of the cadaveric temporal bones. In FIG. 12C, for example, the defects inlude a defect 160 in the superior semicircular canal with a head of a malleus bone 162 visible through the tegmen defects. A standard high resolution (0.625 mm slice thickness) CT scan of the cadaveric temporal bones is then performed. FIG. 14 shows an exemplary CT scan with a large tegmen defect 164 overlying the head of a malleus bone.

From the CT images, virtual 3D models of the cadaveric temporal bones are created using commercially available CAD (Computer Aided Design) modeling software (MATERIALISE™, Leuven, Belgium) using bone windows for segmentation. These models depict the temporal bones with high fidelity. Due to challenges with signal averaging even with high resolution clinical CT, the exact dimensions of the known defects are not identically represented, however the contour of the entire middle fossa floor is well defined in the 3D models, as shown in FIGS. 15A and 15B, wherein FIG. 15A shows an actual cadaveric temporal bone and FIG. 15B shows a 3D model representation of the cadaveric temporal bone shown in FIG. 15A.

Figure 16A:
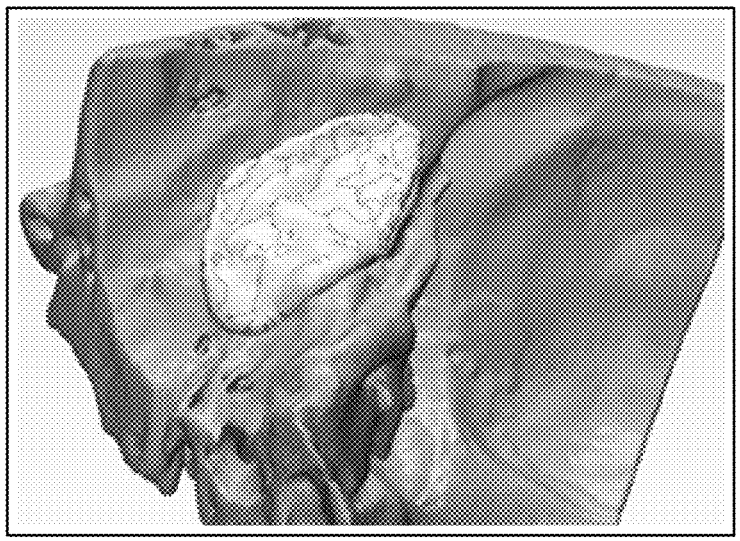
FIG. 16A is a first view of a 3D model of a cadaveric temporal bone with the designed reconstruction tegmen plate showing a precise fit between the temporal bone and reconstruction tegmen plate.
Figure 16B:
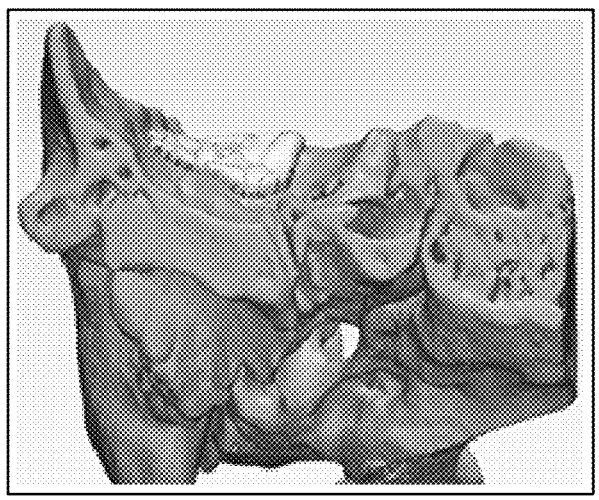
FIG. 16B is a second view of a 3D model of a cadaveric temporal bone with the designed reconstruction tegmen plate showing a precise fit between the temporal bone and reconstruction tegmen plate.
Figure 16C:
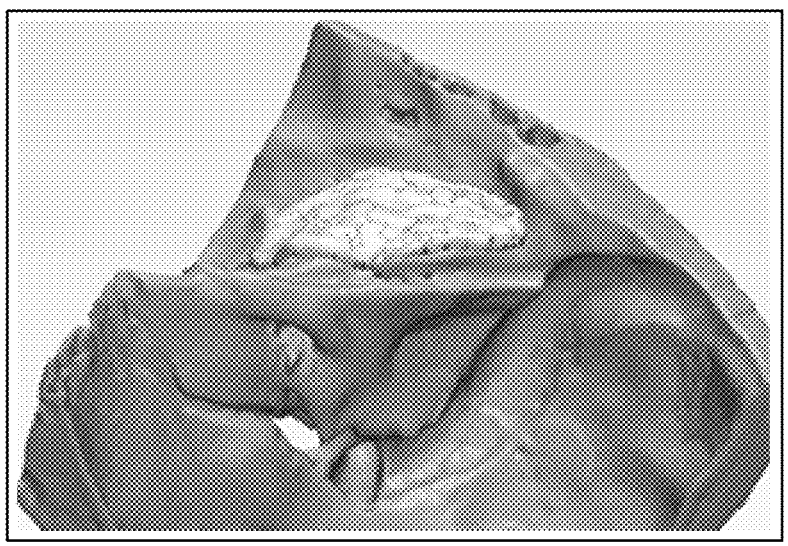
FIG. 16C is a third view of a 3D model of a cadaveric temporal bone with the designed reconstruction tegmen plate showing a precise fit between the temporal bone and reconstruction tegmen plate.

From the virtual 3D models, prosthetic tegmen plates are designed at 1.5 mm thickness, exactly contoured to the shape of the middle fossa floor, and designed to cover all defects in detail. FIGS. 16A, 16B, and 16C show representative views of a 3D model having a virtual prosthetic tegmen plate.

Figure 17A:
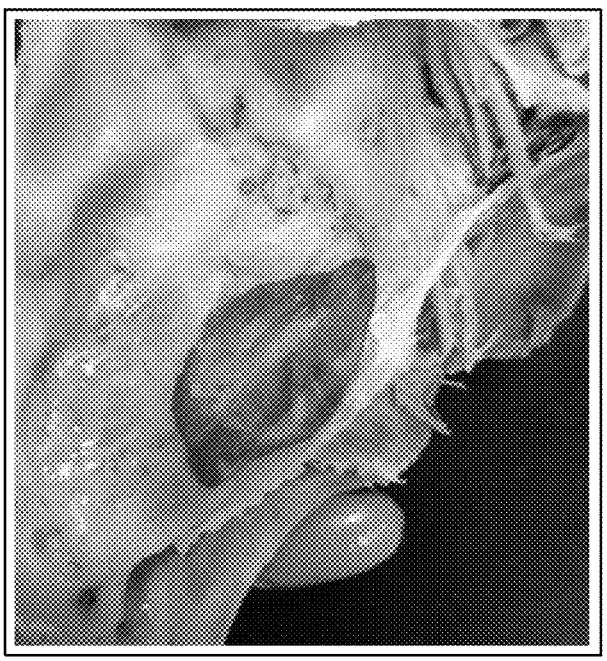
FIG. 17A is a photograph of a left cadaveric temporal bone with a 3D-printed reconstruction prosthetic tegmen plate in place viewed from cephalad.
Figure 17B:
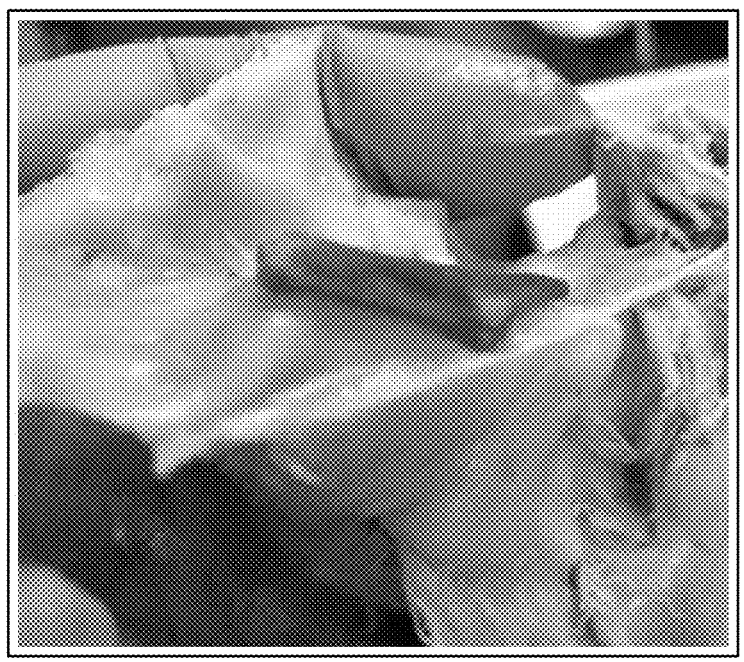
FIG. 17B is a posterior view of a prosthetic tegmen plate disposed on a temporal bone, wherein the prosthetic tegmen plate hugs the contours of the temporal bone.

The virtual prosthetic tegmen plates are then 3-dimensionally printed first in a rigid plastic on a fused deposition modeling printer. The printed tegmen plates are then applied to the surfaces of the cadaveric temporal bones. Each of the designs demonstrates exceptional fit to the cadaveric bone in which the plates "snapped" into position due to the exact contour matching to the middle fossa. The defects in each of the cadaveric bones are covered completely by the plates. FIGS. 17A and 17B show a left cadaveric temporal bone with a 3D-printed tegmen plate disposed thereon.

Figure 18C:
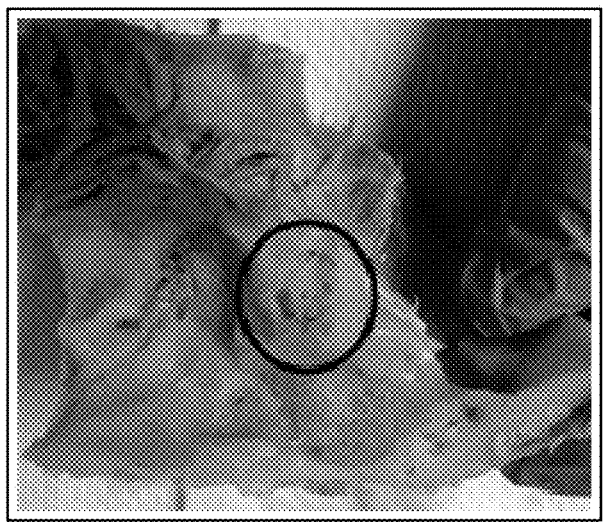
FIG. 18C is a photograph of a third cadaveric temporal bone with a defect shown in the circle.
Figure 18B:
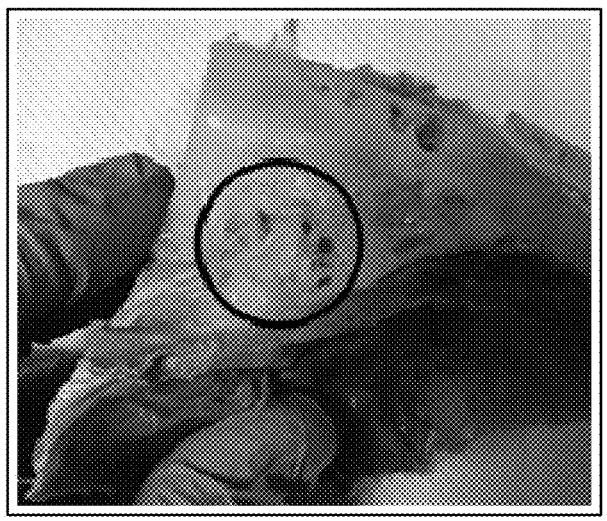
FIG. 18B is a photograph of a second cadaveric temporal bone with a defect shown in the circle.
Figure 18A:
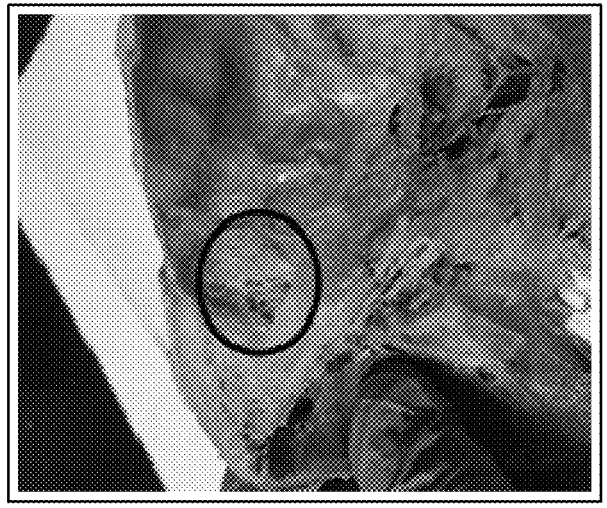
FIG. 18A is a photograph of a first cadaveric temporal bone with a defect shown in the circle.
Figure 18F:
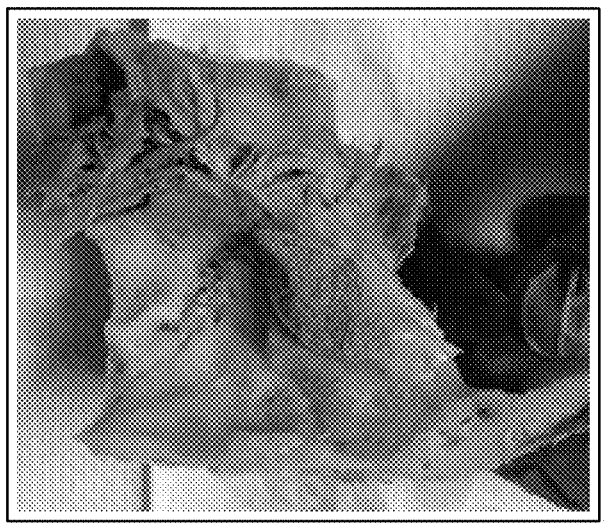
FIG. 18F is a photograph of the temporal bone shown in FIG. 18C with a prosthetic tegmen plate disposed on the temporal bone.
Figure 18E:
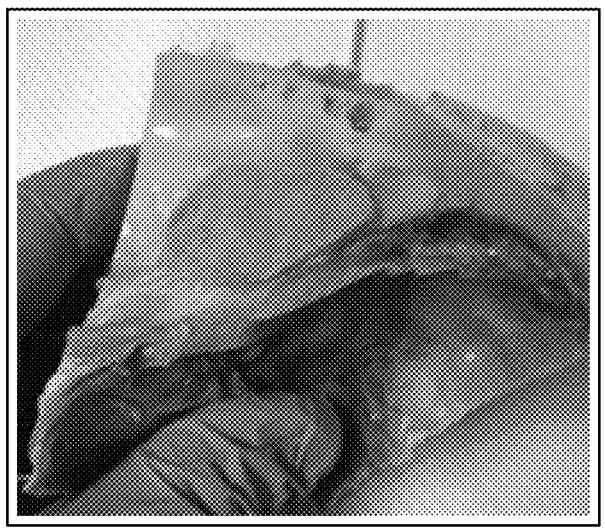
FIG. 18E is a photograph of the temporal bone shown in FIG. 18B with a prosthetic tegmen plate disposed on the temporal bone.
Figure 18D:
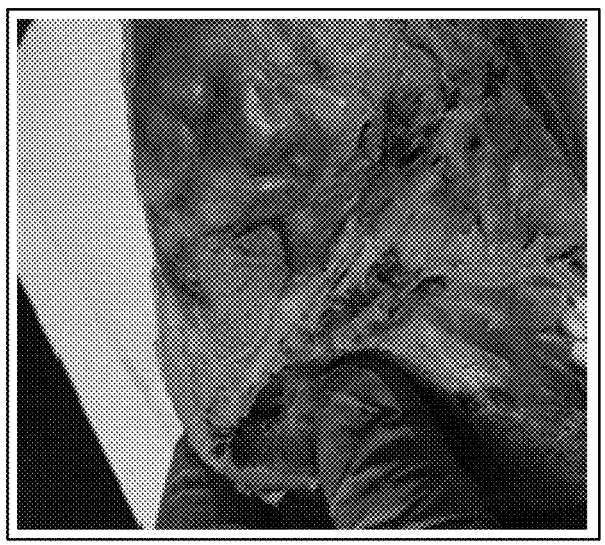
FIG. 18D is a photograph of the temporal bone shown in FIG. 18A with a prosthetic tegmen plate disposed on the temporal bone.

The designs, i.e., virtual 3D models, for the cadaveric plates are submitted to Oxford Performance Materials (OPM; South Windsor, Conn.). Prosthetic tegmen plates are then 3-dimensionally printed via the pre-defined selective laser sinter (SLS) printing process in the FDA-approved material poly-ether-ketone-ketone (PEKK). Design specifications are verified and final prints are laser scanned for accuracy. The prosthetic tegmen plates are then fitted to the surface of the 3 cadaveric temporal bones; again demonstrating exceptional fit with the target design process and material. FIGS. 18A, 18B, and 18C show the three temporal bones and associated defects and FIGS. 18D, 18E, and 18F show the same temporal bones with prosthetic tegmen plates disposed thereon.

Example 2

Figure 19A:
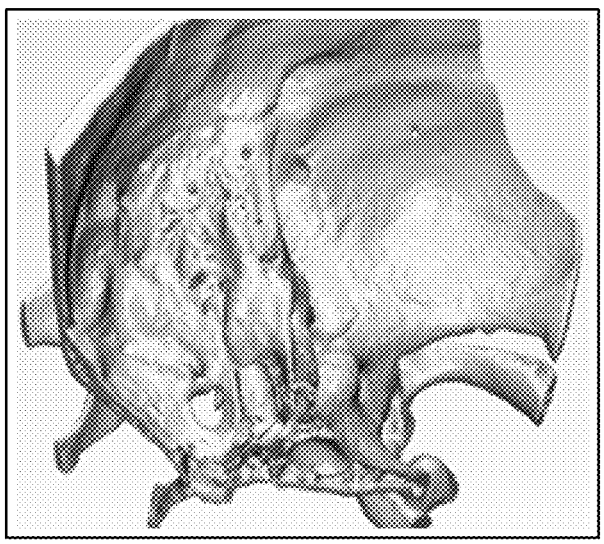
FIG. 19A shows a 3D model of a patient's temporal bone.
Figure 19B:
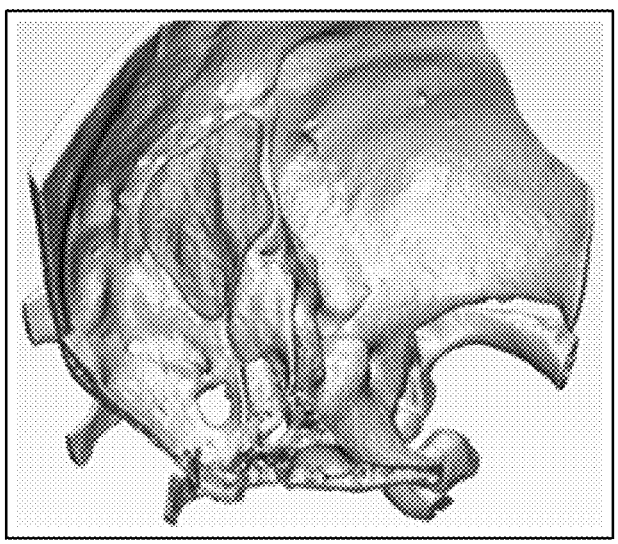
FIG. 19B shows a 3D model shown in FIG. 19A with a virtual prosthetic tegmen plate in situ.
Figure 19C:
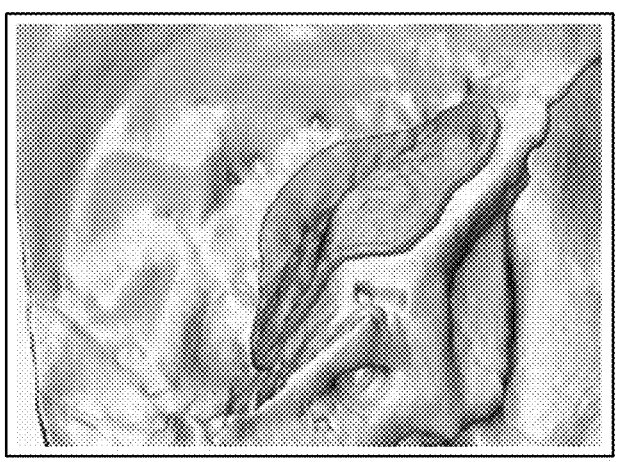
FIG. 19C shows a close-up view of the 3D model of FIG. 19B and shows exact contour matching of the prosthetic tegmen plate to the temporal bone.

A prosthetic tegmen plate is made for a patient having a tegmen defect. The prosthetic tegmen plate is designed for the patient in an identical fashion to the cadaveric temporal bones described in Example 1. FIG. 19A shows a model of the patient's temporal bone, and FIGS. 19B and 19C show views of a designed tegmen plate disposed on the temporal bone of FIG. 19A. A model of the patient's temporal bone as well as two different sized prosthetic tegmen plates at 1.5 mm thickness are then 3-dimensionally printed with the FDA-approved PEKK printing system with OPM. Institutional review board (IRB) approval is obtained for a trial placement during the traditional middle fossa repair of the patient's tegmen defect.

Figure 20C:
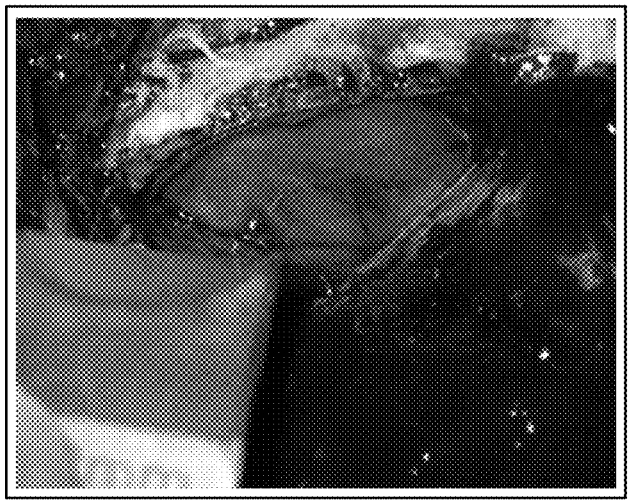
FIG. 20C is an intraoperative photograph of the middle fossa shown in FIG. 20A with the defects covered with pre-cut dural substitute.
Figure 20B:
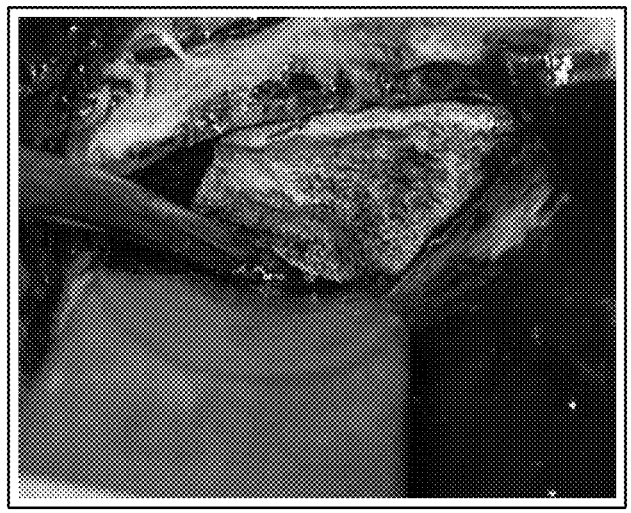
FIG. 20B is an intraoperative photograph of the middle fossa shown in FIG. 20A with a 3D printed prosthetic tegmen plate disposed over the defects and covering the defects entirely.
Figure 20A:
FIG. 20A shows an intraoperative photograph of a middle fossa, wherein elevation of dura off the middle fossa floor reveals the defects in the tegmen.

IRB approval allows for temporary intraoperative placement to test fit to the patient's temporal bone. The prosthetic tegmen plates and temporal bone model are first sterilized using traditional autoclave parameters. As shown in FIG. 20A, a middle cranial fossa approach is then performed in standard fashion and dura is elevated exposing the tegmen defects. Next, the 3D printed prosthetic tegmen plate is gently inserted atruamatically. This is very easily performed and again the prosthetic tegmen plate snap-fitted into position as the cadaveric bones had demonstrated with an exact match to the tegmen contour, as shown in FIG. 20B. Placement of this prosthetic tegmen plate requires 48 seconds. Next, the 3D printed prosthetic tegmen plate is removed and a traditional reconstruction using a dural substitute (DURAGEN® dural regeneration matrix) is performed. This procedure required 3 minutes and 16 seconds, but it is noted that the dural substitute is pre-cut to fit across the involved tegmen based on the 3D printed temporal bone model. This pre-fabrication step from the 3D printed construct saved significant time modifying and cutting the dural substitute to fit precisely. FIG. 20C shows the tegmen repair performed with the dural substitute. The temporal lobe is gently replaced onto the middle fossa floor, the bone flap fixated into anatomical position, and the wound closed in standard layered fashion.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:
1. A prosthetic tegmen plate comprising:
   a prefabricated solid and unitary plate formed by additive manufacturing and comprising a biocompatible material, the plate defining:
      at least one edge;
      an unmodified portion extending inwardly from the at least one edge towards a central portion, the unmodified portion having a length of at least 2 mm and having at least one engagement surface configured to substantially conform to a region of a corresponding superior surface of a subject's temporal bone surrounding a tegmen defect, and the central portion configured to span, cover, and be elevated over the tegmen defect, wherein the central portion is elevated by a height of greater than or equal to 0.05 mm to less than or equal to 1 mm relative to the unmodified portion, wherein the prosthetic tegmen plate is configured to be both nestingly mateable to the corresponding superior surface of the subject's temporal bone in a single orientation and securable to the temporal bone of the subject with a snap fit between the superior surface of the subject's temporal bone and the at least one engagement surface.

2. The prosthetic tegmen plate according to claim 1, wherein the prosthetic tegmen plate has a thickness of less than or equal to about 5 mm.

3. The prosthetic tegmen plate according to claim 1, wherein the biocompatible material is selected from the group consisting of: a biocompatible polymer, a ceramic, a metal, and combinations thereof.

4. The prosthetic tegmen plate according to claim 3 wherein the biocompatible material is a non-bioresorbable polymer selected from the group consisting of a polyaryl ether ketone (PAEK), poly(methyl acrylate) (PMA), poly (methyl methacrylate) (PMMA), polyetherimide (PEI), polysulfone, polyphenolsulfone, copolymers thereof, and combinations thereof.

5. The prosthetic tegmen plate according to claim 4, wherein the PAEK is selected from the group consisting of polyetherketone (PEK), polyether ketone ketone (PEKK), polyether ether ketone (PEEK), polyether ether ketone ketone (PEEKK), polyether ketone ether ketone ketone (PEKEKK), and combinations thereof.

6. The prosthetic tegmen plate according to claim 3, wherein the biocompatible material is polyether ketone ketone (PEKK).

7. The prosthetic tegmen plate according to claim 1, wherein the biocompatible material is a bioresorbable biocompatible polymer.

8. The prosthetic tegmen plate according to claim 7, wherein the biocompatible material further comprises at least one component selected from the group consisting of: a growth factor, a suspension of cells, an anti-inflammatory agent, an antimicrobial agent, a blood fraction, and combinations thereof.

9. The prosthetic tegmen plate according to claim 1, wherein the biocompatible material is a bioresorbable polymer selected from the group consisting of poly lactic acid (PLA), poly glycolic acid (PGA), poly lactic co-glycolic acid (PLGA), polyhydroxybutyrate (PHB), polyhydroxyvalerate (PHV), poly(desaminotyrosyl-tyrosine ethyl carbonate) (poly(DTE-carbonate)), polycaprolactone, polyanhydrides, polyorthoesters, copolymers thereof, and combinations thereof.

10. The prosthetic tegmen plate according to claim 1, wherein the biocompatible material comprises a material selected from the group consisting of starch, alginate, hyaluronic acid, collagen, fibrin, silk, and combinations thereof.

11. The prosthetic tegmen plate according to claim 1, wherein the prosthetic tegmen plate is securable to the temporal bone of the subject without use of anchoring hardware or adhesives.

12. The prosthetic tegmen place according to claim 1, wherein the solid, rigid, and unitary plate has a thickness of greater than or equal to about 0.5 mm to less than or equal to about 2 mm, and the central portion is elevated by a height of greater than or equal to about 0.2 mm to less than or equal to about 0.7 mm.

13. A prosthetic tegmen plate comprising:
a solid, rigid, and unitary plate defining:
at least one edge;
an unmodified portion extending inwardly from the at least one edge towards a central portion, the unmodified portion having a length of at least 2 mm and having an engagement surface configured to substantially conform to a region of a corresponding superior surface of a subject's temporal bone surrounding a tegmen defect, the engagement surface being configured to be nestingly mateable to the corresponding superior surface of the subject's temporal bone in a single orientation; and
the central portion being configured to span, and be elevated over the tegmen defect, wherein the central portion is elevated by a height of greater than or equal to 0.05 mm to less than or equal to 1 mm relative to the unmodified portion,
wherein the prosthetic tegmen plate is securable to the corresponding superior surface of the subject's temporal bone as the solid, rigid, and unitary plate.

14. The prosthetic tegmen plate according to claim 13, wherein the prosthetic tegmen plate is prefabricated relative to a surgical procedure.

15. The prosthetic tegmen plate according to claim 13, wherein the prosthetic tegmen plate is securable to the corresponding superior surface of the subject's temporal bone without using anchoring hardware or adhesives.

16. A method of implanting a prosthetic tegmen plate in a subject having a tegmen defect, the method comprising:
implanting a prosthetic tegmen plate in the subject so as to cover the tegmen defect, wherein the prosthetic tegmen plate comprises a prefabricated solid and unitary plate defining at least one edge, an unmodified portion extending inwardly from the at least one edge towards a central portion, the unmodified portion having a length of at least 2 mm and having at least one engagement surface configured to substantially conform to a region of a corresponding superior surface of the subject's temporal bone surrounding the tegmen defect, and the central portion configured to span, cover, and be elevated over the tegmen defect, wherein the central portion is elevated by a height of greater than or equal to 0.05 mm to less than or equal to 1 mm relative to the unmodified portion, wherein the prosthetic tegmen plate comprises a biocompatible material and is generated by additive manufacturing from a three dimensional (3D) model created from preoperative images of the subject's temporal bone, is configured to be nestingly mineable to the corresponding superior surface of the subject's temporal bone in a single orientation and to be securable to the temporal bone of the subject with a snap fit between the superior surface of the subject's temporal bone and the at least one engagement surface, so that the at least one engagement surface substantially conforms to the corresponding superior surface of the subject's temporal bone after the implanting.

17. The method according to claim 16, wherein implanting the prosthetic tegmen plate in the subject comprises locating the prosthetic tegmen plate in the subject such that the at least one engagement surface nestingly mates with the corresponding superior surface of the subject's temporal bone without requiring any anchoring with hardware or adhesives.

18. The method according to claim 16, further comprising generating the prosthetic tegmen plate before the implanting, the generating comprising:
    creating a first three dimensional (3D) model of the tegmen defect from preoperative images of the subject's temporal bone;
    creating a second 3D model of the prosthetic tegmen plate complementary to the first 3D model; and
    additive manufacturing the prosthetic tegmen plate from the second 3D model, wherein the at least one engagement surface of the prosthetic tegmen plate is complementary to at least a portion of a superior surface of the subject's temporal bone comprising the tegmen based on the first 3D model.

19. The method according to claim 16, wherein the preoperative images are created by magnetic resonance imaging (MRI), computed tomography (CT), positron emission tomography (PET), ultrasound, X-ray, or a combination thereof.

20. The method according to claim 16, wherein the prosthetic tegmen plate is generated by 3D printing.

21. The method according to claim 16, wherein the implanting comprises:
    creating a window through a parietal bone of the subject;
    exposing the tegmen defect; and
    implanting the prosthetic tegmen plate on the subject's temporal bone, such that the prosthetic tegmen plate covers the subject's tegmen defect.

22. The method according to claim 16, wherein implanting further comprises sealing the prosthetic tegmen implant in place with a layer of the subject's fascia.

23. The method according to claim 16, wherein the prosthetic tegmen plate further comprises at least one supplemental component selected from the group consisting of a growth factor, a suspension of cells, an anti-inflammatory agent, an antimicrobial agent, a blood fraction, and combinations thereof.

24. The method according to claim 16, wherein the tegmen defect is associated with a congenital defect, intracranial hypertension, pulsatile tinnitus, tullio phenomenon, encephalocele, a cerebrospinal fluid (CSF) leak, or meningitis.

25. The method according to claim 16, wherein the tegmen defect is a defect in the subject's tegmen tympani, tegmen mastoideum, or combination thereof.

26. A method of manufacturing the prosthetic tegmen implant of claim 1, the method comprising:
    generating a first three dimensional (3D) model of at least a portion of the subject's temporal bone comprising the tegmen defect from preoperative images of the subject's temporal bone;
    designing a second 3D model of the prosthetic tegmen plate such that the at least one engagement surface is complimentary to at least a portion of the subject's temporal bone comprising the tegmen defect; and
    generating the prosthetic tegmen plate such that the at least one engagement surface substantially conforms to the corresponding superior surface of the subject's temporal bone.

27. The method according to claim 26, wherein the generating of the first 3D model and the second 3D model occurs by use of image processing software.

28. The method according to claim 26, wherein generating a prosthetic tegmen plate comprises generating a prosthetic tegmen plate by additive manufacturing.

29. The method according to claim 26, wherein the designing a second 3D model of a prosthetic tegmen plate comprises:
    drawing a two dimensional outline of the prosthetic tegmen implant over the tegmen defect on the first 3D model, the two dimensional outline defining edges of the prosthetic tegmen implant; and
    offsetting the two dimensional outline to generate a virtual 3D tegmen plate construct having a thickness of at least about 1 mm.

30. The method according to claim 29, further comprising, prior to the offsetting:
    elevating a central portion of the two dimensional outline off of the tegmen defect to a height of from greater than or equal to about 0.05 to less than or equal to about 1 mm,
    wherein the two dimensional outline has an unmodified portion that extends inward from the edges toward the central portion and the unmodified portion having a length of at least about 2 mm.

* * * * *